United States Patent
Edwards et al.

(10) Patent No.: US 9,944,879 B2
(45) Date of Patent: Apr. 17, 2018

(54) PHOSPHOROUS-CONTAINING COMPOUNDS AND USES THEREOF

(71) Applicant: Afton Chemical Corporation, Richmond, VA (US)

(72) Inventors: David Edwards, Richmond, VA (US); Bevin Parks, Midlothian, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 14/681,507

(22) Filed: Apr. 8, 2015

(65) Prior Publication Data

US 2016/0102266 A1 Apr. 14, 2016

Related U.S. Application Data

(60) Provisional application No. 62/061,470, filed on Oct. 8, 2014.

(51) Int. Cl.
| | | |
|---|---|---|
| *C10M 137/10* | (2006.01) | |
| *C07F 9/165* | (2006.01) | |
| *C10M 137/00* | (2006.01) | |
| *C10M 143/00* | (2006.01) | |
| *C07F 9/16* | (2006.01) | |
| *C10M 137/04* | (2006.01) | |

(52) U.S. Cl.
CPC ........... *C10M 137/105* (2013.01); *C07F 9/16* (2013.01); *C07F 9/1652* (2013.01); *C10M 137/00* (2013.01); *C10M 137/04* (2013.01); *C10M 143/00* (2013.01); *C10M 2223/04* (2013.01); *C10M 2223/047* (2013.01); *C10N 2230/06* (2013.01); *C10N 2230/10* (2013.01); *C10N 2230/12* (2013.01); *C10N 2240/04* (2013.01); *C10N 2240/08* (2013.01); *C10N 2240/10* (2013.01); *C10N 2240/12* (2013.01)

(58) Field of Classification Search
CPC .............. C10M 137/00; C10M 143/00; C10M 137/105; C10M 137/04; C10M 2223/04; C10M 2223/047; C07F 9/16; C07F 9/1652; C10N 2230/06; C10N 2230/10; C10N 2230/12; C10N 2240/04; C10N 2240/08; C10N 2240/10; C10N 2240/12
See application file for complete search history.

(56) References Cited

U.S. PATENT DOCUMENTS

| | | | |
|---|---|---|---|
| 5,132,031 A | 7/1992 | Born | |
| 5,306,436 A | 4/1994 | Born | |
| 5,463,132 A * | 10/1995 | Born | C07F 9/091 568/22 |
| 5,919,965 A * | 7/1999 | Gentles | C07B 59/004 544/243 |
| 6,043,305 A * | 3/2000 | Harris | C07F 9/4075 252/609 |

FOREIGN PATENT DOCUMENTS

| | | |
|---|---|---|
| GB | 821 937 A | 10/1959 |
| GB | 1329978 * | 9/1993 |
| JP | S60 23491 A | 2/1985 |

OTHER PUBLICATIONS

European Search Report for EP 15 18 8742, dated Dec. 8, 2015.

* cited by examiner

*Primary Examiner* — Cephia D Toomer
(74) *Attorney, Agent, or Firm* — Brinks Gilson & Lione

(57) ABSTRACT

The present invention provides phosphorous-containing compounds useful as antiwear additive components, lubricant additive compositions and lubricant compositions each comprising such compounds, and methods for making and using the same.

44 Claims, No Drawings

PHOSPHOROUS-CONTAINING COMPOUNDS AND USES THEREOF

CROSS REFERENCE TO RELATED APPLICATIONS

This application claims the benefit of U.S. Provisional Application No. 62/061,470 filed Oct. 8, 2014, the entire contents of which is hereby incorporated herein by reference.

FIELD OF THE INVENTION

The invention relates to phosphorous-containing compounds useful as antiwear additive components, lubricant additive compositions and lubricant compositions each comprising such compounds, and methods for making and using the same.

BACKGROUND OF THE INVENTION

Traditionally, anti-wear components of lubricating compositions comprise acidic organophosphates salted with amines and/or metal ions. These components provide good anti-wear protection but other performance attributes can suffer including poor seal durability, reduced oxidative stability, and inadequate corrosion inhibition. Phosphorus- and sulfur-containing compounds are understood to be essential in lubricating fluids to protect surfaces from wear as a result of the extreme pressures encountered by the surfaces. As a result, these fluids have traditionally been harmful to seals (dynamic and static) and yellow metals. In addition, there is increasing pressure from regulatory agencies to remove amines and metal ions from lubricating fluids to decrease the environmental impact of such components. Due to these increasing environmental concerns, the presence of amines and metal ions in antiwear additives is becoming less desirable. Accordingly, there is a need to develop novel antiwear compounds that do not contain amines or metal ions.

BRIEF SUMMARY OF THE INVENTION

In one aspect, the invention relates to a compound of Formula (I):

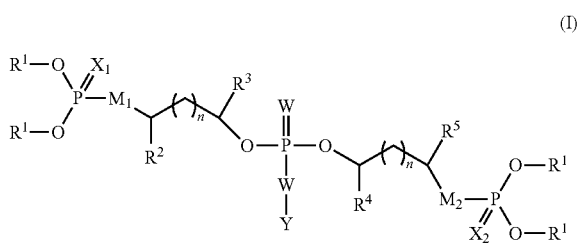

(I)

wherein each $R^1$ is independently alkyl or cycloalkyl;
each of $R^2$ $R^3$, $R^4$ and $R^5$ is independently selected from the group consisting of hydrogen, alkyl and cycloalkyl;
each n is independently an integer from 0 to 6;
$M_1$, $M_2$, $X_1$, and $X_2$ are each independently S or O;
each W is independently S or O;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In a second aspect, the invention provides a compound prepared by reacting a compound of the structure

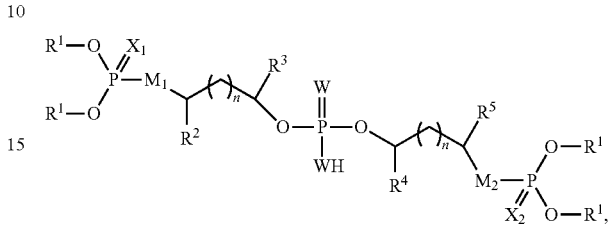

with a reactive group to form a compound of the structure

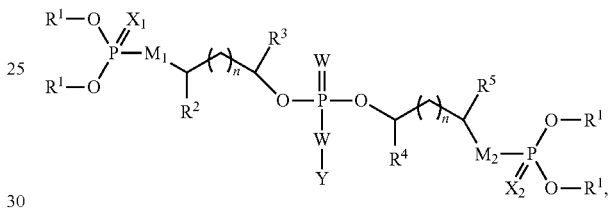

wherein each W is independently S or O;
$M_1$, $M_2$, $X_1$, and $X_2$ are each independently S or O;
each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In a third aspect, the invention provides a lubricant additive composition comprising a compound of the present invention.

In a fourth aspect, the invention provides a lubricant composition comprising a major amount of an oil of lubricating viscosity or a grease prepared therefrom and a minor amount of the compound of the present invention.

In a fifth aspect, the invention provides a method of lubricating moving metal surfaces comprising lubricating the metal surfaces with a lubricant composition of the present invention.

In a sixth aspect, the invention provides a method of increasing the oxidative stability of a lubricating composition comprising adding to the lubricant composition an effective amount of a compound of the present invention.

DETAILED DESCRIPTION OF THE INVENTION

The invention disclosed herein relates to novel phosphorous-containing compounds that are useful as antiwear agents and methods for preparing the same. The invention also provides lubricant additive compositions and lubricant compositions comprising the compounds, and methods of using the same.

The compounds of the present invention include the compounds of Formula (I)

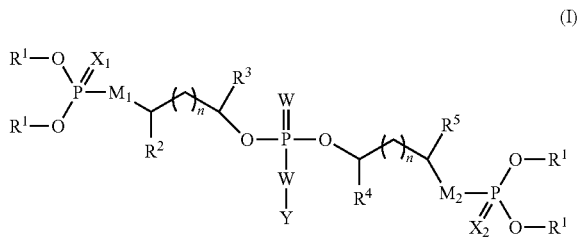

wherein each $R^1$ is independently alkyl or cycloalkyl;
$R^2$ $R^3$, $R^4$ and $R^5$ is independently selected from the group consisting of hydrogen, alkyl and cycloalkyl;
each n is independently an integer from 0 to 6;
$M_1$, $M_2$, $X_1$, and $X_2$ are each independently S or O;
each W is independently S or O;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In one embodiment, $X_1$ is S.
In one embodiment, $X_2$ is S.
In another embodiment, $M_1$ is S.
In another embodiment, $M_2$ is S.
In a further embodiment, $X_1$, $X_2$, $M_1$, and $M_2$ are each S.
In another embodiment, $X_1$ is O.
In another embodiment, $X_2$ is O.
In another embodiment, $M_1$ is O.
In another embodiment, $M_2$ is O.
In a further embodiment, $X_1$, $X_2$, $M_1$ and $M_2$ are each O.
In one embodiment, $X_1$ and $X_2$ are O and $M_1$ and $M_2$ are S.
In another embodiment, $X_1$ and $X_2$ are S and $M_1$ and $M_2$ are O.
In another embodiment, each $R^2$ $R^3$, $R^4$ and $R^5$ is independently selected from hydrogen or $C_1$-$C_{30}$ alkyl.
In a further embodiment, each W is O. In another embodiment, each W is S. In yet another embodiment, one W is S and the other W is O.

In one embodiment, each $R^1$ is independently selected from $C_1$-$C_{30}$ alkyl. In another embodiment, each $R^1$ is independently selected from $C_3$-$C_{10}$ alkyl. In another embodiment, each $R^1$ is independently selected from $C_3$-$C_6$ alkyl. In certain embodiments, each $R^1$ is the same as every other $R^1$.

In another embodiment, at least one of $R^2$ and $R^3$ is hydrogen and at least one of $R^4$ and $R^5$ is hydrogen.
In another embodiment, $R^2$, $R^3$, $R^4$ and $R^5$ are hydrogen.
In one embodiment, Y is $C_1$-$C_{20}$ alkyl.
In certain embodiment, $R^3$ and $R^4$ are the same.
In another embodiment, $R^2$ and $R^5$ are the same.
In another embodiment, $R^2$ and $R^4$ are the same.
In another embodiment, $R^3$ and $R^5$ are the same.

In a further embodiment, $R^2$ and $R^5$ are both hydrogen.
In another embodiment, one of $R^2$ and $R^3$ and one of $R^4$ and $R^5$ is $C_1$-$C_{10}$ alkyl.
In one embodiment, the invention provides a compound of Formula (I), wherein the compound is a compound of Formula (IA)

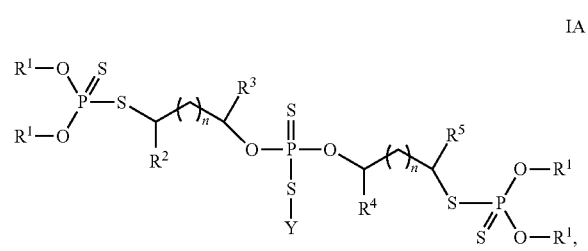

wherein each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In another embodiment, the invention provides a compound of Formula (I), wherein the compound is a compound of Formula (IB)

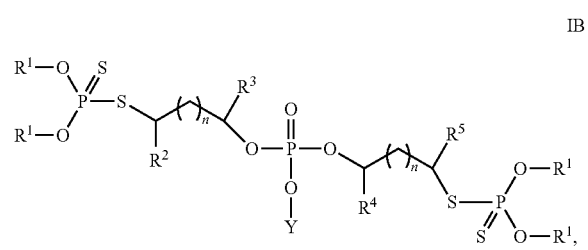

wherein each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In one embodiment, the invention provides a compound selected from:
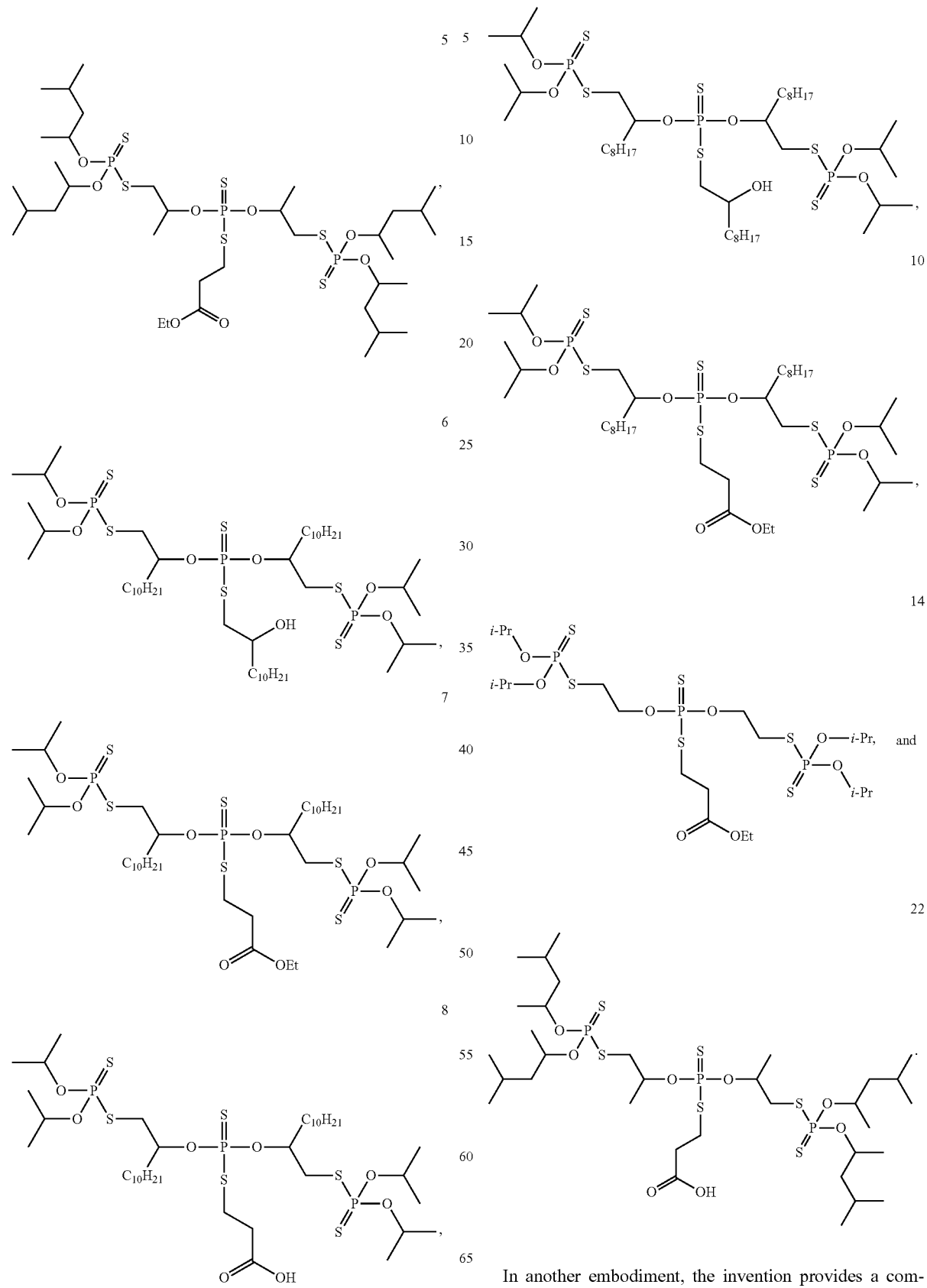
In another embodiment, the invention provides a compound selected from:

5
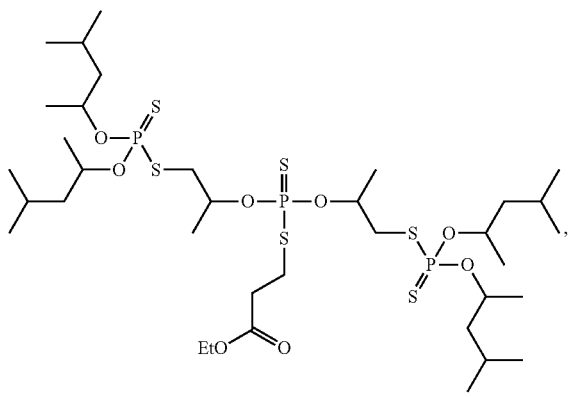
6
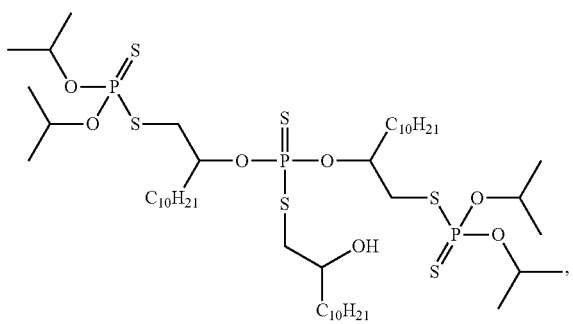
9
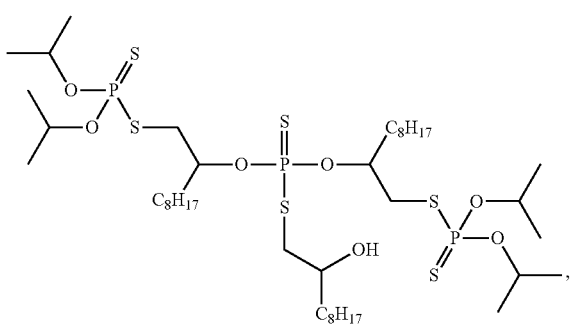
10
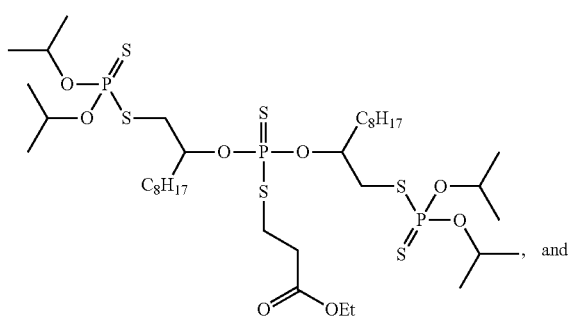, and
22
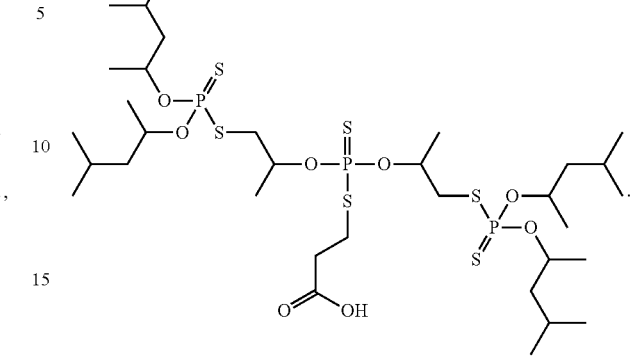.
In another embodiment, the invention provides a compound selected from:
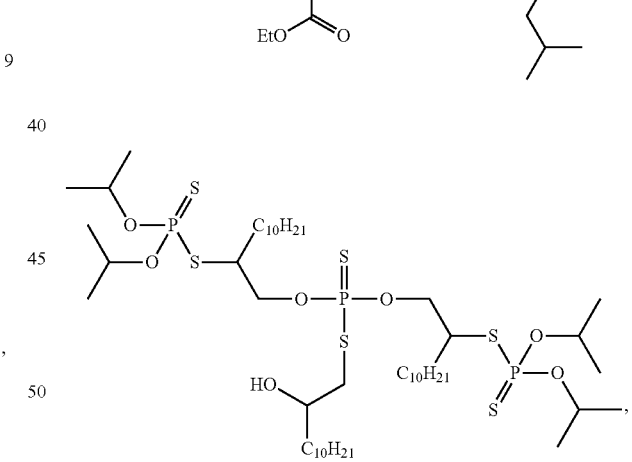
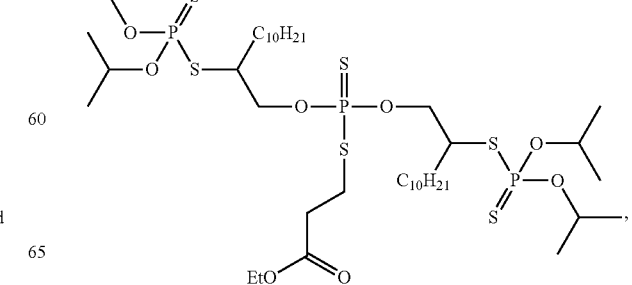,

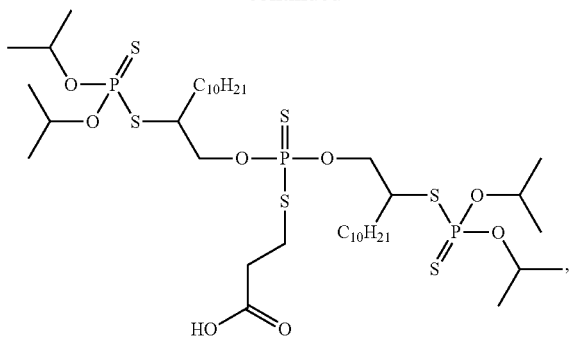
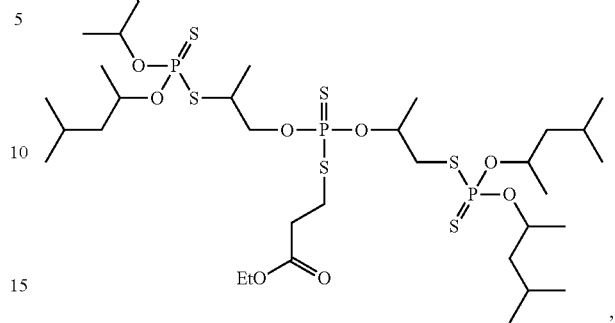
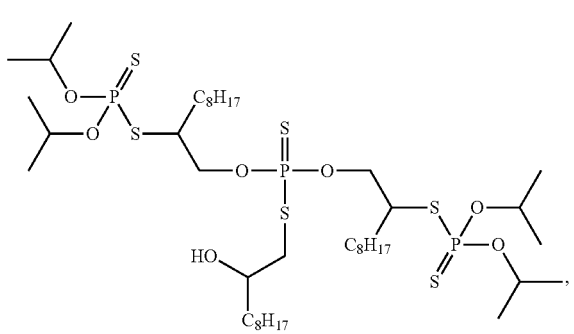
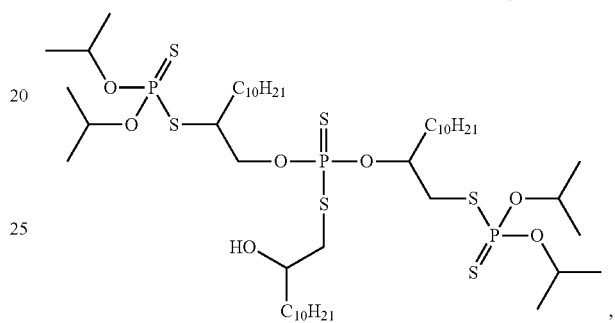
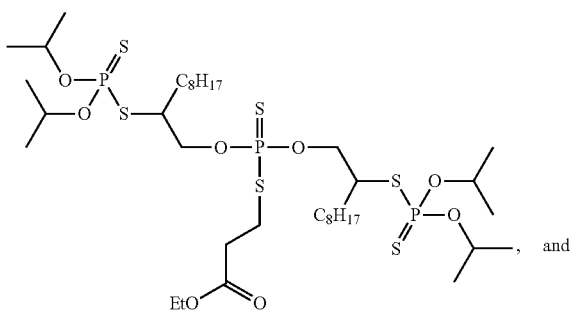
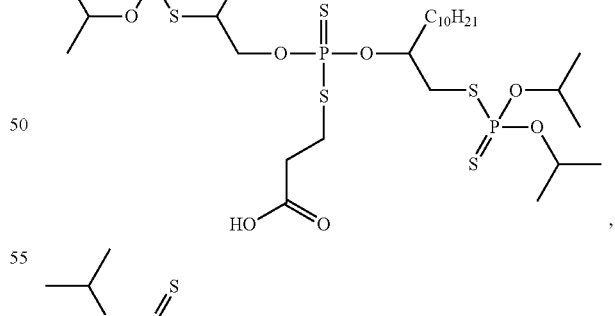
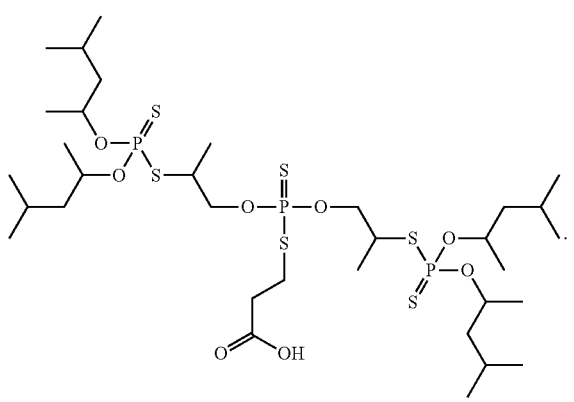
In a further embodiment, the invention provides a compound selected from:

-continued

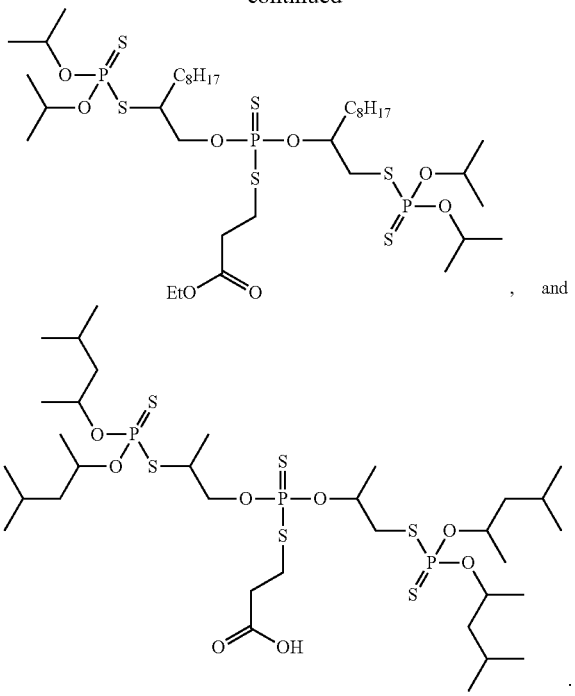

, and

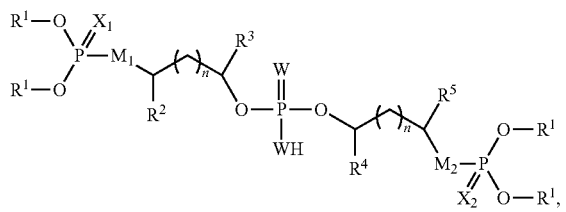

In one aspect, the invention provides a compound prepared by reacting a compound of the formula:

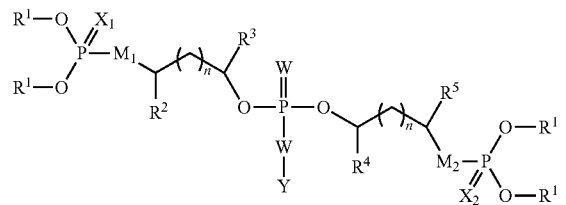

with a reactive group to form a compound of the structure wherein each W is independently S or O;
$M_1$, $M_2$, $X_1$, and $X_2$ are each independently S or O;
each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

In a further embodiment, the invention provides a compound prepared by a process comprising:
(a) reacting a compound of the formula:

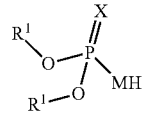

with an epoxide of the formula

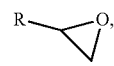

wherein R is alkyl or cycloalkyl; and
M and X are each independently S or O;
(b) reacting the reaction product of step (a) with $P_2W_5$, to form a compound of the structure

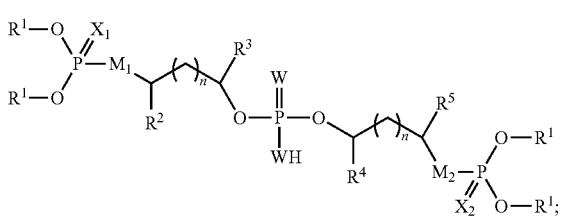

and
(c) reacting the reaction product of step (b) with a reactive group to form a compound of the structure

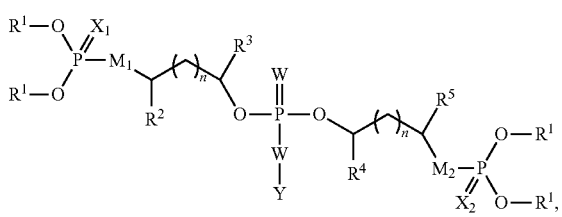

wherein
$M_1$, $M_2$, $X_1$, and $X_2$ are each independently S or O;
each W is the same and is S or O;
each $R^2$ $R^3$, $R^4$ and $R^5$ is independently selected from the group consisting of hydrogen, alkyl and cycloalkyl;
n is 0;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

As used herein, the term "alkyl," as well as the as the alkyl moieties of other groups referred herein (e.g., alkoxyl) may be a linear or branched chain saturated hydrocarbon containing from 1 to 30 carbon atoms.

As used herein, the term "substituted" refers to wherein one or more hydrogen atoms are each independently replaced with a non-hydrogen substituent.

As used herein, the term "alkoxy" refers to an alkyl group attached to the parent molecular moiety through an oxygen atom.

As used herein, the term "alkoxyalkylene" refers to a group -alkylene-O-alkyl.

As used herein, the term "alkylene" refers to a methylene or polymethylene group, i.e., $-(CH_2)_z-$, wherein z is a positive integer from 1 to 30.

As used herein the term "hydroxyalkylene" refers to the group $R^a-R^b-$ wherein $R^a$ is HO— and $R^b$ is alkylene.

As used herein the term "hydroxyalkyleneoxy" refers to the group $R^a-R^b-R^c$ wherein $R^a$ is HO—, $R^b$ is alkylene and $R^c$ is —O—.

As used herein, the phrase "reactive group" refers to an electrophilic chemical group that is capable of attaching a carbon atom of a substituent to a sulfur atom in a nucleophilic P—SH group, for example, in a dithiophosphate, or attaching a carbon atom of a substituent to an oxygen atom of a nucleophilic P—OH, for example, in a phosphate. Such reactive groups are readily recognized by those skilled in the art. Examples of suitable reactive groups in accordance with the present invention include alkyl halides, activated alkyl alcohols including tosylates, triflates and mesylates, epoxides, and acrylate derivatives. In certain embodiments, the reactive group can be selected from 1-bromohexadecane, methyl iodide, benzyl bromide, vinyl butyl ether, ethyl acrylate, 1,2-epoxydodecane, acrylic acid, 1,2-epoxydecane, and 2-hydroxyethyl acrylate.

As used herein, the phrase "effective amount" means an amount sufficient to provide the desired effect. For example, the compounds of the present invention are useful as antiwear agents when incorporated into lubricant compositions. Therefore, an effective amount of a compound of the present invention when incorporated into a lubricant composition can be an amount that improves the antiwear properties of the lubricant compositions comprising a compound of the instant invention as compared to the same lubricant composition that does not comprise a compound of the instant invention.

As used herein, the terms "oil composition," "lubrication composition," "lubricating composition," "lubricating oil composition," "lubricating oil," "lubricant composition," "fully formulated lubricant composition," and "lubricant" are considered synonymous, fully interchangeable terminology referring to the finished lubrication product comprising a major amount of a base oil plus a minor amount of an additive composition.

The compounds of the present disclosure include all stereoisomers (e.g., cis and trans isomers) and all optical isomers of compounds of Formula I (e.g., R and S enantiomers), certain positional isomers, as well as racemic, diastereomeric and other mixtures of such isomers. Those skilled in the relevant art can readily envision such isomers and the isomers are included within the scope of the present invention.

The compounds, salts and proadditives of the present disclosure can exist in several tautomeric forms, including the enol and imine form, and the keto and enamine form and geometric isomers and mixtures thereof. All such tautomeric forms are included within the scope of the present disclosure. Even though one tautomer may be described, the present disclosure includes all tautomers of the present compounds.

The compounds of the present invention are contemplated to be used as an additive in lubricating base oil. As used herein, the term "base oil" refers to oils categorized by the American Petroleum Institute (API) category groups Group I-V oils as well as animal oils, vegetable oils (e.g. castor oil and lard oil), petroleum oils, mineral oils, synthetic oils, and oils derived from coal or shale. The American Petroleum Institute has categorized these different basestock types as follows: Group I, greater than 0.03 wt percent sulfur, and/or less than 90 vol percent saturates, viscosity index between 80 and 120; Group II, less than or equal to 0.03 wt percent sulfur, and greater than or equal to 90 vol percent saturates, viscosity index between 80 and 120; Group III, less than or equal to 0.03 wt percent sulfur, and greater than or equal to 90 vol percent saturates, viscosity index greater than 120; Group IV, all polyalphaolefins. Hydrotreated basestocks and catalytically dewaxed basestocks, because of their low sulfur and aromatics content, generally fall into the Group II and Group III categories. Polyalphaolefins (Group IV basestocks) are synthetic base oils prepared from various alpha olefins and are substantially free of sulfur and aromatics.

Groups I, II, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may sometimes be referred to as synthetic fluids in the industry.

The compounds of the present invention can be added to base oils in the form of a mineral oil or synthetic oil, animal oil, vegetable oil, or mixtures thereof. In general, the mineral oils, both paraffinic and naphthenic and mixtures thereof can be employed as lubricating oil or as the grease vehicle. Also contemplated are greases in which any of the foregoing oils are employed as a base.

The compound of the present invention, in addition to other additive components, can be added to a lubricating oil to form a finished fluid having a viscosity of at least an SAE 90 or 75W-85. Viscosity indexes from about 95 to 130 being preferred. The average molecular weights of these oils can range from about 250 to about 800.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

Where synthetic oils, or synthetic oils employed as the vehicle for the grease, are desired in preference to mineral oils, or in mixtures of mineral and synthetic oils, various synthetic oils may be used. Typical synthetic oils include polyisobutylenes, polybutenes, polydecenes, siloxanes and silicones (polysiloxanes).

The present invention provides lubricant compositions comprising a major amount of oil of lubricating viscosity or a grease prepared therefrom and a minor amount of a compound of the present invention. The compound of the present invention can be in the lubricant composition in an amount between about 0.001% to 10%, between 0.01% to 5%, between 0.01% to 1.0%, between 0.5% to 2.0%, and between 0.015% to about 0.5% by weight of the total composition. In some embodiments, lubricating compositions can contain between about from 0.01% to 0.5%, between about 0.01 and about 0.4 wt %, or between about 0.01 and about 0.3 wt %, or between about 0.01 and about 0.2 wt %.

As mentioned above, the compounds of the present invention can be readily formulated into lubricant compositions suitable for use with a variety of machine parts and components. The lubricant compositions comprising a compound of the present invention can optionally further comprise one or more other additive components such that the lubricant compositions. The list of additive components disclosed below is not exhaustive and additive components not expressly disclosed herein are well known to the skilled artisan and may also be included in the lubricant compositions. Without limitation, additive components that can be used in the lubricant compositions of the present invention include antioxidants, additional antiwear agents, corrosion inhibitors, detergents, extreme pressure agents, viscosity index improvers, and friction reducers.

In one embodiment, the lubricant composition of the present invention comprises a compound of the present invention and at least one additional additive composition selected from the group consisting of an antioxidant, antiwear agents, corrosion inhibitor, detergent, extreme pressure agent, dispersant, viscosity index improvers, and friction modifiers.

The compounds of the present invention can be incorporated into an oil of lubricating viscosity directly. Alternatively, compounds of the present invention can be prepared in combination with other lubricant additives to form a lubricant additive composition. Generally, the lubricant additive composition will further be incorporated into the oil of lubricating viscosity at a particular wt % of the lubricant additive package relative to the total weight of the final lubricant composition. The wt % selected is generally referred to as the treat rate and the lubricant composition containing the lubricant additive composition is generally referred to as a finished fluid.

In one embodiment the present invention provides a lubricant additive composition comprising a compound of the present invention and at least one additional additive component. The one or more additional additive component(s) can be selected from an antioxidant, antiwear agents, corrosion inhibitor, detergent, extreme pressure agent, viscosity index improvers, and friction modifiers.

Antioxidants

Antioxidant compounds are known and include, for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. A single antioxidant or a combination of two or more can be used.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In an embodiment the hindered phenol antioxidant may be an ester and may include, e.g., an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight of the antioxidant, based upon the final weight of the lubricating oil composition. In some embodiments, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In an embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

The one or more antioxidant(s) may be present in ranges of from about 0 wt. % to about 20 wt. %, or about 0.1 wt. % to about 10 wt. %, or about 1 wt. % to about 5 wt. %, of the lubricating composition.

Antiwear Agents

Examples of additional suitable antiwear agents include, but are not limited to, a metal thiophosphate; a metal dialkyldithiophosphate; a phosphoric acid ester or salt thereof; a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. The phosphorus containing antiwear agents are more fully described in European Patent No. 0612 839. The metal in the dialkyl dithio phosphate salts may be an alkali metal, alkaline earth metal, aluminum, lead, tin, molybdenum, manganese, nickel, copper, titanium, or zinc. A useful antiwear agent may be a zinc dialkyldithiophosphate.

The antiwear agent may be present in ranges of from about 0 wt. % to about 15 wt. %, or about 0.01 wt. % to about 10 wt. %, or about 0.05 wt. % to about 5 wt. %, or about 0.1 wt. % to about 3 wt. % of the total weight of the lubricating composition.

Detergents

The lubricant composition may optionally comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds and methylene bridged phenols. Suitable detergents and their methods of preparation are described in greater detail in numerous patent publications, including U.S. Pat. No. 7,732,390, and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. A suitable detergent may include alkali or alkaline earth metal salts of petroleum sulfonic acids and long chain mono- or di-alkylarylsulfonic acids with the aryl group being one of benzyl, tolyl, and xylyl.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, the MR, is greater than one. Such salts are commonly referred to as overbased, hyperbased, or superbased salts and may be salts of organic sulfur acids, carboxylic acids, or phenols.

The overbased detergent may have a metal ratio of from 1.1:1, or from 2:1, or from 4:1, or from 5:1, or from 7:1, or from 10:1.

In some embodiments, a detergent can be used for reducing or preventing rust in a gear, axle, or engine.

The detergent may be present at about 0 wt. % to about 10 wt. %, or about 0.1 wt. % to about 8 wt. %, or about 1 wt. % to about 4 wt. %, or greater than about 4 wt. % to about 8 wt. % based on the total weight of the lubricant composition.

Dispersants

The lubricant composition may optionally further comprise one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless-type dispersants are characterized by a polar group attached to a relatively high molecular or weight hydrocarbon chain. Typical ashless dispersants include N-substituted long chain alkenyl succinimides. Examples of N-substituted long chain alkenyl succinimides include polyisobutylene succinimide with number average molecular weight of the polyisobutylene substituent in a range of about 350 to about 5000, or about 500 to about 3000. Succinimide dispersants and their preparation are disclosed, for instance in U.S. Pat. No. 7,897,696 and U.S. Pat. No. 4,234,435. Succinimide dispersants are typically an imide formed from a polyamine, typically a poly(ethyleneamine).

In some embodiments the lubricant composition comprises at least one polyisobutylene succinimide dispersant derived from polyisobutylene with number average molecular weight in the range about 350 to about 5000, or about 500 to about 3000. The polyisobutylene succinimide may be used alone or in combination with other dispersants.

In some embodiments, polyisobutylene (PIB), when included, may have greater than 50 mol %, greater than 60 mol %, greater than 70 mol %, greater than 80 mol %, or greater than 90 mol % content of terminal double bonds. Such a PIB is also referred to as highly reactive PIB ("HR-PIB"). HR-PIB having a number average molecular weight ranging from about 800 to about 5000 is suitable for use in embodiments of the present disclosure. Conventional non-highly reactive PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable. Such an HR-PIB is commercially available, or can be synthesized by the polymerization of isobutene in the presence of a non-chlorinated catalyst such as boron trifluoride, as described in U.S. Pat. No. 4,152,499 and U.S. Pat. No. 5,739,355. When used in the aforementioned thermal ene reaction, HR-PIB may lead to higher conversion rates in the reaction, as well as lower amounts of sediment formation, due to increased reactivity.

One class of suitable dispersants may be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may be high molecular weight esters or half ester amides.

The dispersants may also be post-treated by conventional methods by reaction with any of a variety of agents. Among these agents are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. No. 7,645,726; U.S. Pat. No. 7,214,649; and U.S. Pat. No. 8,048,831 describe some suitable post-treatment methods and post-treated products.

The dispersant, if present, can be used in an amount sufficient to provide up to about 20 wt. %, based upon the total weight of the lubricating oil composition. The amount of the dispersant that can be used may be about 0.1 wt. % to about 15 wt. %, or about 0.1 wt. % to about 10 wt. %, or about 3 wt. % to about 10 wt. %, or about 1 wt. % to about 6 wt. %, or about 7 wt. % to about 12 wt. %, based upon the total weight of the lubricating oil composition. In an embodiment, the lubricating oil composition utilizes a mixed dispersant system.

Extreme Pressure Agents

The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated waxes; organic sulfides and polysulfides such as dibenzyldisulfide, bis(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Friction Modifiers

The lubricating oil compositions herein may also optionally contain one or more additional friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanidines, alkanolamides, phosphonates, metal-containing compounds, glycerol esters, sulfurized fatty compounds and olefins, sunflower oil and other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In a embodiments the friction modifier may be a long chain fatty acid ester. In an embodiment the long chain fatty acid ester may be a mono-ester, or a di-ester, or a (tri)glyceride. The friction modifier may be a long chain fatty amide, a long chain fatty ester, a long chain fatty epoxide derivative, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g. carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291.

A friction modifier may be present in amounts of about 0 wt. % to about 10 wt. %, or about 0.01 wt. % to about 8 wt. %, or about 0.1 wt. % to about 4 wt. %, based on the total weight of the lubricant composition.

Viscosity Index Improvers

The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 2012/0101017 A1.

The lubricating oil compositions herein also may optionally contain one or more dispersant viscosity index improvers in addition to a viscosity index improver or in lieu of a viscosity index improver. Suitable dispersant viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt. % to about 20 wt. %, about 0.1 wt. % to about 15 wt. %, about 0.1 wt. % to about 12 wt. %, or about 0.5 wt. % to about 10 wt. % based on the total weight, of the lubricating composition.

Effective amounts of the various additive components for a specific formulation may be readily ascertained, but for illustrative purposes these general guides for representative effective amounts are provided. The amounts below are given in weight % of the finished fluid.

| Component | Example Ranges (wt %) | Example Ranges (wt %) |
| --- | --- | --- |
| A compound of the present invention | 0-10 | 0.3-5 |
| Dispersant | 0-20 | 0.5-8 |
| Extreme Pressure Agent | 0-5 | 2-4 |
| Rust Inhibitor | 0-1.0 | 0.05-1.0 |

| Component | Example Ranges (wt %) | Example Ranges (wt %) |
|---|---|---|
| Corrosion Inhibitor | 0-5 | 0.05-3 |
| Demulsifier | 0-5 | 0.005-1.0 |
| Antifoam Agent | 0-0.5 | 0.001-0.1 |
| Diluent | 0-10 | 1.0-5.0 |
| Lubricating Base Oil | Balance | Balance |

The compounds of the present invention, and lubricant additive compositions comprising the same, can be used in automotive gear or axle oils. Typical of such oils are automotive spiral-bevel and worm-gear axle oils which operate under extreme pressures, load and temperature conditions, hypoid gear oils operating under both high speed, low-torque and low-speed, high torque conditions.

Industrial lubrication applications in which the compounds of the present invention, and lubricant additive compositions comprising the same, can be used include hydraulic oils, industrial gear oils, slideway machines oils, circulation oils and steam turbine oils, gas turbine oils, for both heavy-duty gas turbines and aircraft gas turbines, way lubricants, gear oils, compressor oils, mist oils and machine tool lubricants. Engine oils are also contemplated such as passenger car motor oils, heavy duty diesel engine oils, marine engine oils, locomotives, and high speed automotive diesel engines.

Functional fluids can also be prepared from the compounds of the present invention and lubricant additive compositions comprising the same. These fluids include automotive fluids such as manual transmission fluids, automatic transmission fluids, continuously variable transmission fluids, power steering fluids and power brake fluids.

Compounds of the present invention can also be incorporated into greases such as automotive, industrial and aviation greases, and automobile chassis lubricants.

The invention also provides a method of lubricating metal surfaces. Lubricating metal surfaces with lubricant compositions of the present invention can reduce wear between the metal surfaces when moving. In one embodiment, the metal surfaces being lubricated can be a machine part. The machine part can comprise an axle, a differential, an engine, a manual transmission, an automatic transmission, a continuously variable transmission, a clutch, a hydraulic apparatus, an industrial gear, a slideway apparatus, and a turbine.

The invention further provides for a method of lubricating a driveline, industrial, or metalworking device comprising lubricating the driveline, industrial or metalworking device with a lubricant composition comprising a compound of the present invention.

The invention further provides a method for increasing oxidative stability of a lubricating composition comprising adding to the composition an effective amount of a compound of the present invention.

Although certain embodiments of the present invention may be described individually herein, it is understood by the skilled artisan that any one embodiment can be combined with any other embodiment or embodiments, and is contemplated by the scope of the instant invention.

Synthetic Schemes

Certain compounds of the present invention can be prepared using the following generic schemes. Unless otherwise indicated, the atoms and substituents indicated in the following schemes have the same meanings as given to the same atoms and substituents in the above description of the invention.

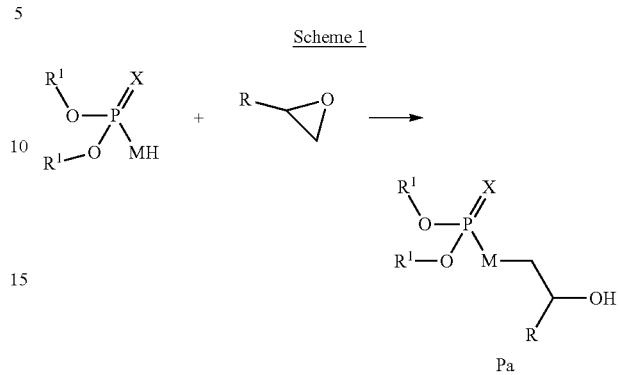

Scheme 1

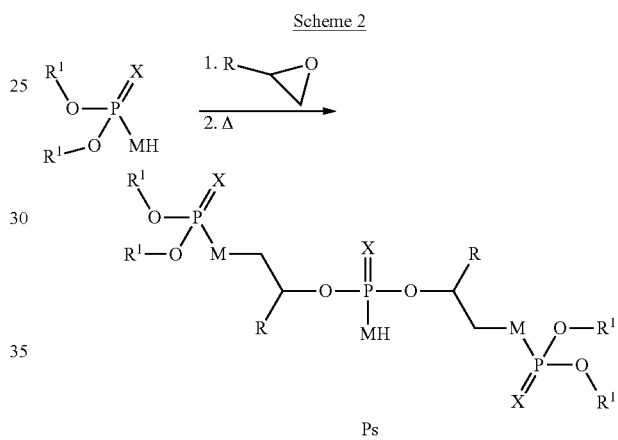

Scheme 2

X and M = O or S; R = alkyl or cycloaklyl.

In certain instances, the synthesis of compounds can result in the production of positional isomers. For example, both primary and secondary alcohols can be formed by a single reaction as follows:

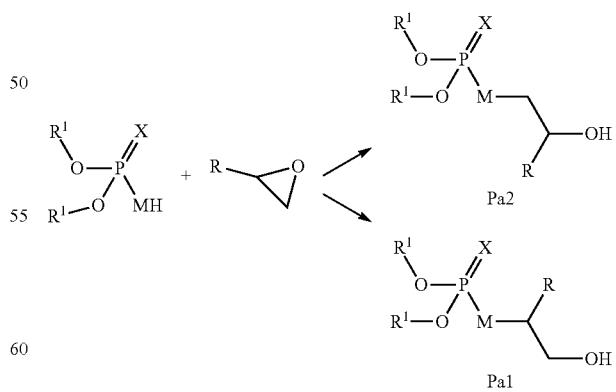

X and M = O or S; R = alkyl or cycloaklyl.

The structures shown in the Intermediates and Examples below are the structures of the most abundant isomers produced in the particular reactions described. The skilled artisan appreciates and understands that the above epoxide addition reaction and reactions similar thereto produce compounds, such as Intermediate Pa as shown above, as secondary alcohols (Pa2). However, the same epoxide addition reaction can form some amount of primary alcohols (Pa1). Therefore, the resulting product of the epoxide addition reactions can be a mixture of positional isomers. For the sake of simplicity, only the secondary alcohols and the reaction products therefrom are shown below in Intermediates and Examples. However, all positional isomers of the Intermediates and Examples are within the scope of the invention as a result of these types of reactions.

Intermediate Pa can further be reacted to form compounds Ps or Po. For example, Intermediate Pa can be reacted with $P_2S_5$ to form Ps, or Intermediate Pa can further be reacted with $P_2O_5$ to form Po. One example is shown below.

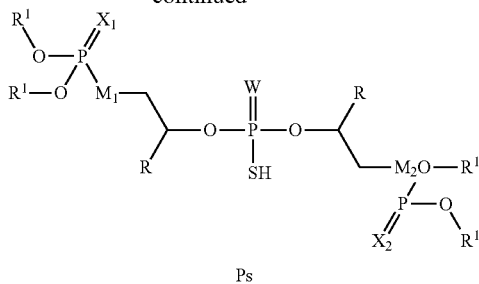

X, W and M = O or S; R = alkyl or cycloalkyl.

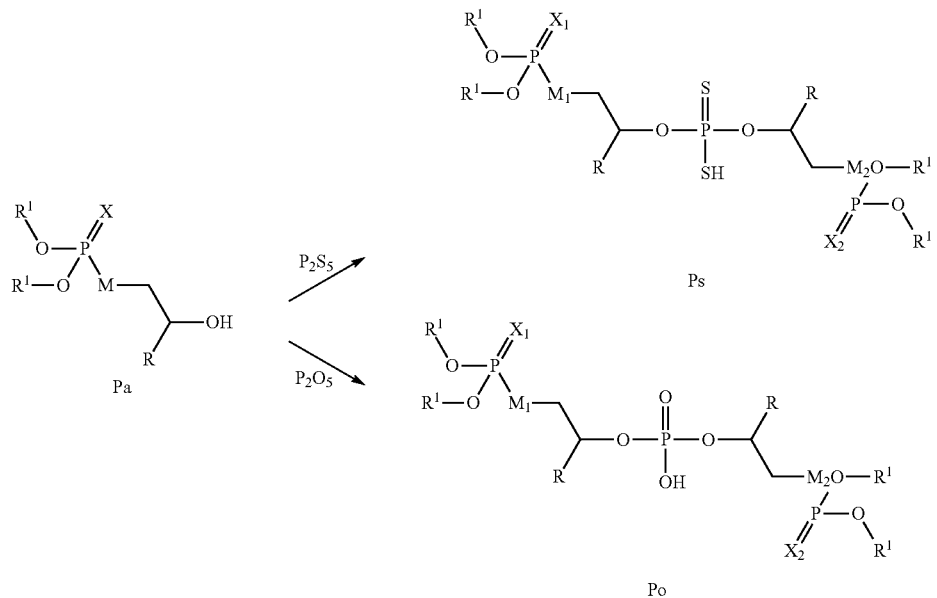

X and M = O or S; alkyl or cycloalkyl.

Pa can also be reacted with Pi to prepare compound Ps as follows:

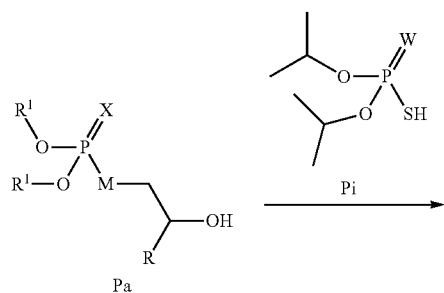

In certain embodiments, the above reaction is carried out at a 2:1 molar ratio Pa:Pi to enhance the yield of Ps as compared to the same reaction carried out in a 1:1 molar ratio.

Similar reaction schemes as those shown above can be used to prepare compounds P3 and P4. For example, when the above reaction schemes are employed, one of $R^2$ and $R^3$ is hydrogen, and one of $R^4$ and $R^5$ is hydrogen. In instances wherein n is greater than zero, the epoxide utilized for forming Pa shown above can be replaced with a halide alcohol, forming intermediate Pa' (not shown). Pa' can further be reacted with O,O-di-isopropyl dithiophosphoric acid to form compound P3.

P3

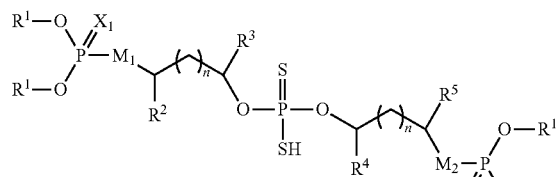

P4

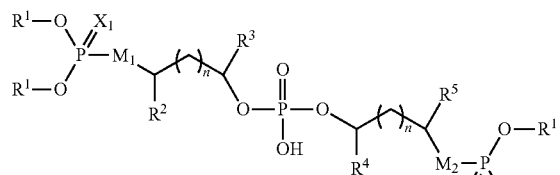

P3 or P4 can further be reacted with a reactive group to prepare compounds of Formula (IA) and Formula (IB), respectively:

IA

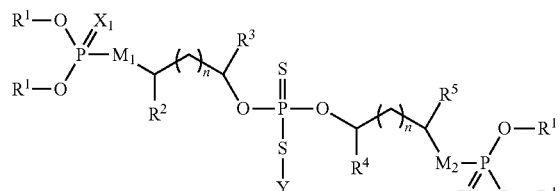

IB

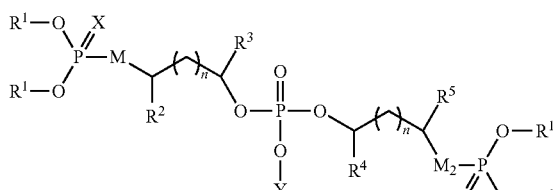

Intermediates such as Pa can also be reacted with POCl3 to form Pc.

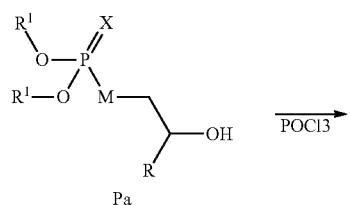 

-continued

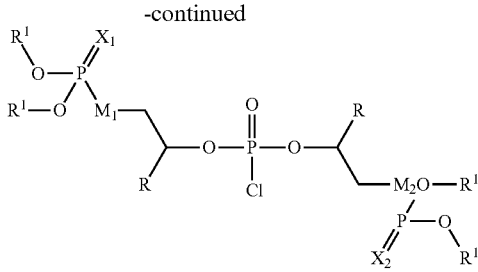

Pc

X, W and M = O or S; R = alkyl or cycloalkyl.

Compounds such as Pc can further be reacted with a nucleophile to form compounds of Formula P4:

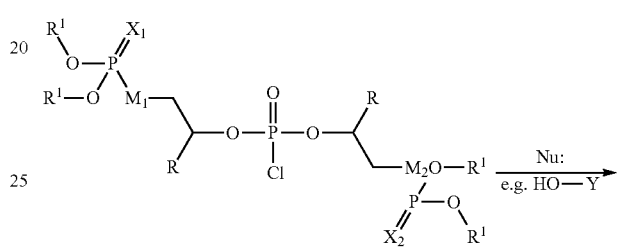

P4

INTERMEDIATES AND EXAMPLES

Unless indicated otherwise, the presence of all Intermediates and Examples was confirmed by 31P NMR.

Intermediates

Synthesis of Intermediate 1a: O,O-bis(4-methylpentan-2-yl) S-hydrogen phosphorodithioate (75.34 g or 0.25 mol) is heated to 40° C. and propylene oxide (14.65 g or 0.25 mol) is added slowly so as to keep the reaction temperature below 50° C. The reaction mixture is then cooked at 50° C. for 30 minutes. Intermediate 1a is the reaction product.

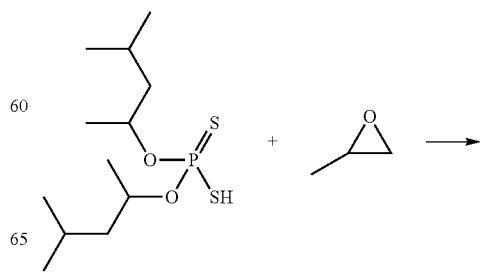

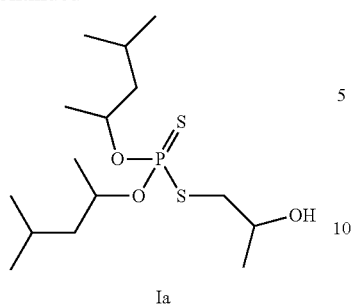

Ia

Synthesis of Intermediate P3-1: Intermediate 1a (1300 g, 3.56 mol) is added to a reaction flask containing P2S5 (198 g, 0.89 mol) and the reaction temperature subsequently brought to 80° C. for 16 hours. The reaction contents are cooled to ambient temperature and unreacted P2S5 removed by filtration. 1406 g of material obtained with a TAN of 65 mg KOH/g.

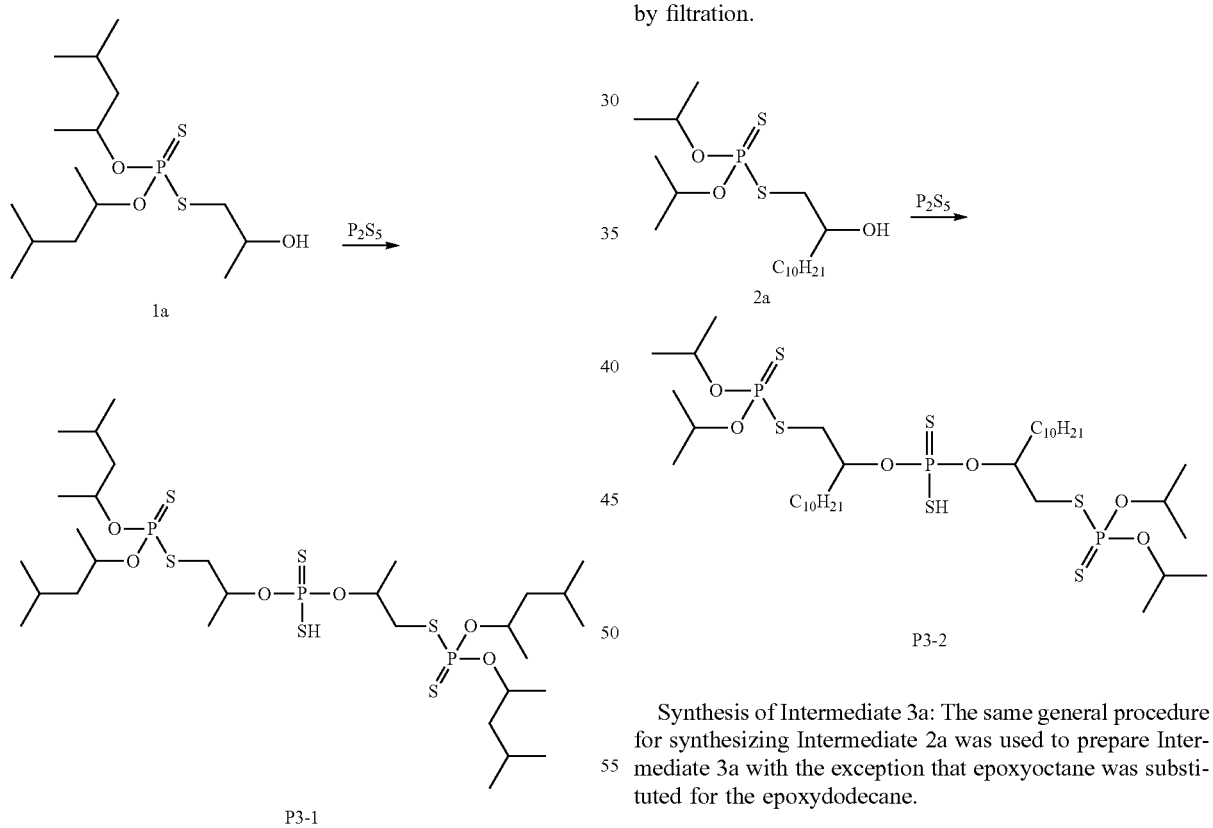

P3-1

Synthesis of Intermediate 2a: 1,2-epoxydodecane (38 g, 207 mmol; supplied by Arkema as Vikolox 12) was added to diisopropyl dithiophosphoric acid (44.1 g, 206 mmol) at an initial temperature of 20° C. at such a rate that the reaction temperature never exceed 30° C. 1H and 31P NMR confirm the consumption of dithiophosphoric acid and the formation of 2a as the product of reaction. LC-MS confirms the structure of Intermediate 2a.

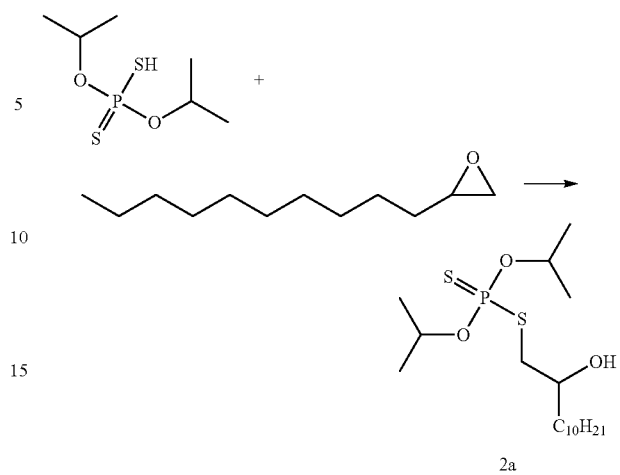

2a

Synthesis of Intermediate P3-2: Intermediate 2a (2023.7 g, 5.08 mol) is added to a reaction flask containing P2S5 (282 g, 1.27 mol) and the reaction temperature subsequently brought to 80° C. for 16 hours. The reaction contents are cooled to ambient temperature and unreacted P2S5 removed by filtration.

P3-2

Synthesis of Intermediate 3a: The same general procedure for synthesizing Intermediate 2a was used to prepare Intermediate 3a with the exception that epoxyoctane was substituted for the epoxydodecane.

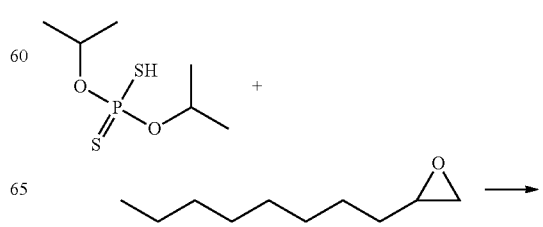

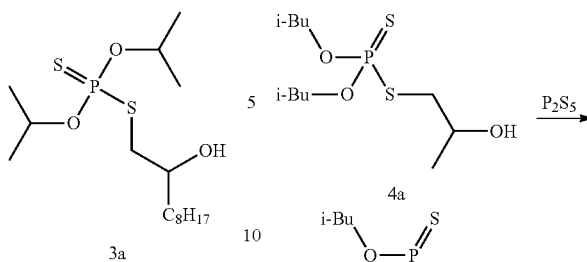

Synthesis of Intermediate P3-3: The same general procedure for synthesizing Intermediate P3-2 was used to prepare Intermediate P3-3. Intermediate P3-3 was characterized by LC-MS and 31P NMR.

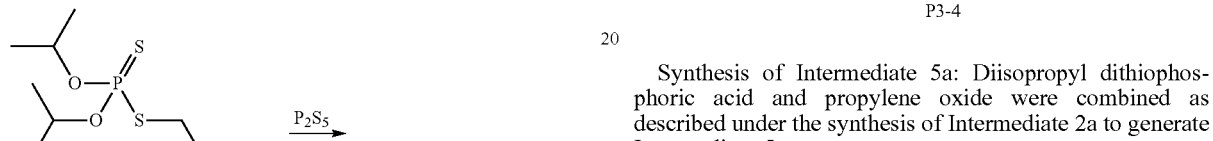

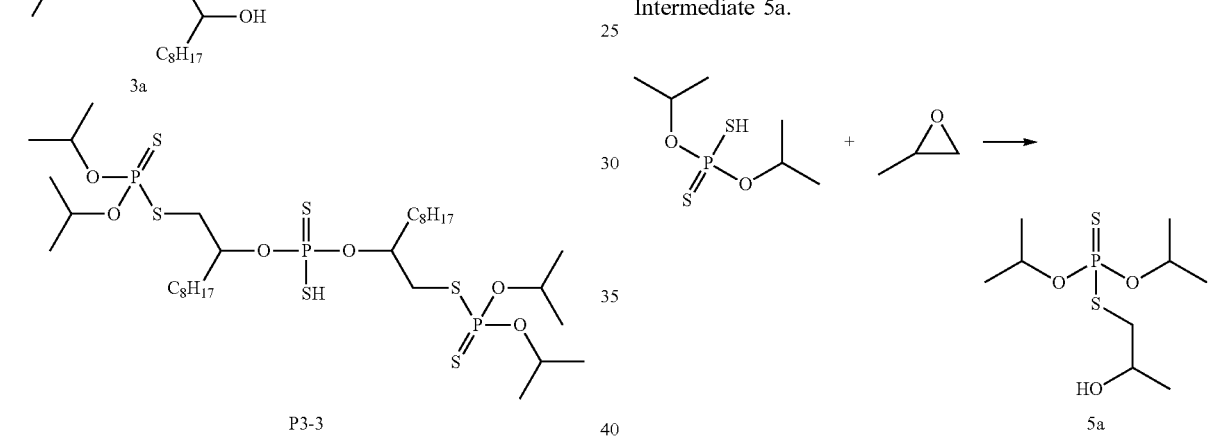

Synthesis of Intermediate 4a: Diisobutyl dithiophosphoric acid and propylene oxide were combined as described under the synthesis of Intermediate 2a.

Synthesis of Intermediate P3-4: Intermediate 4a was reacted with P2S5 to generate P3-4 using the same general procedure as described for P3-2.

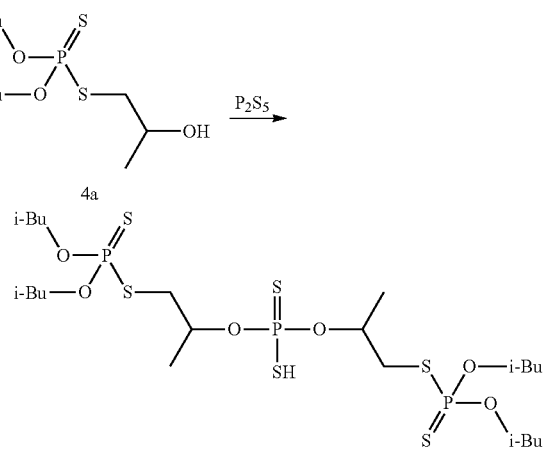

Synthesis of Intermediate 5a: Diisopropyl dithiophosphoric acid and propylene oxide were combined as described under the synthesis of Intermediate 2a to generate Intermediate 5a.

Synthesis of Intermediate P3-5: Intermediate 5a was subsequently reacted with P2S5 to generate P3-5 using the same general procedure as described for P3-2.

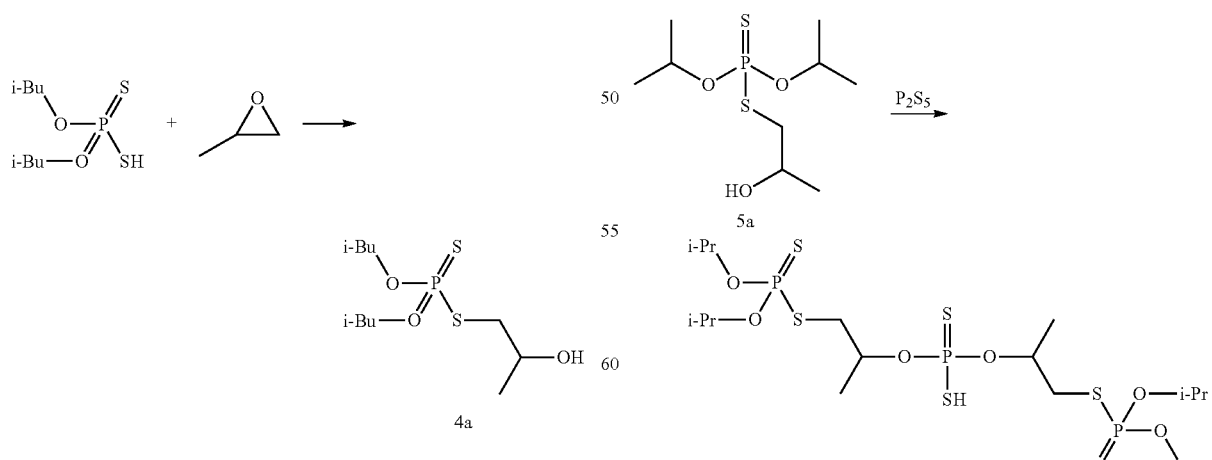

Synthesis of Intermediate 6a: Diisopropyl dithiophosphoric acid (100 g, 0.467 mol) was added to 500 ml of 1 M KOH in water. The reaction contents were stirred until the internal temperature returned to 20° C. and subsequently 2-chloroethanol (50 g, 0.62 mol, Sigma Aldrich 99%) was added. The reaction mixture was heated to reflux for 3.5 hours, cooled to room temperature and the reaction volume doubled with the addition of toluene. The organic layer was collected and the aqueous layer washed twice more with equal volumes of toluene. The combined organic fractions were then washed with a saturated brine solution, dried over magnesium sulfate and filtered. The filtrate was concentrated under reduced pressure to afford 87 g of Intermediate 6a. 1H and 31P NMR confirm the identity of the product as Intermediate 6a.

EXAMPLES

Example 1

To a stirring solution of P3-1 (41.2 g or 0.05 mol) in acetonitrile (35 ml) at 20° C. was added triethylamine (5.3 g or 0.052 mol). The reaction mixture was left to stir without heating for a further five minutes after the addition of amine. Next 1-bromohexadecane (15.7 g or 0.051 mol) was added and the reaction mixture was cooked at 40° C. for 24 hours. The solid precipitate formed was filtered off, washed with heptane and the filtrate concentrated under reduced pressure. 31P NMR confirms the conversion of the P—SH of P3-1 to a P—S-alkyl group.

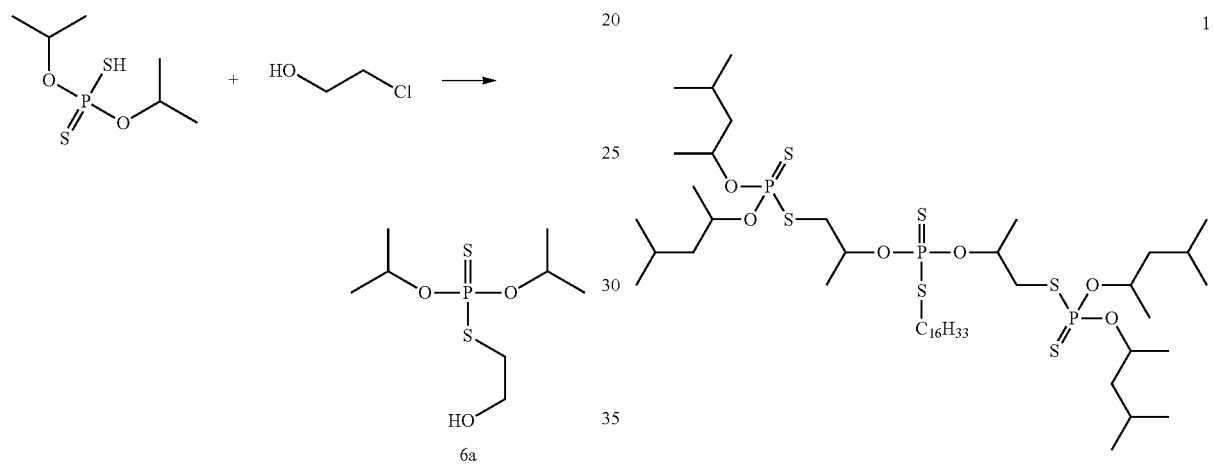

Synthesis of Intermediate P3-6: Intermediate 6a was reacted with P2S5 as described for P3-2 to prepare P3-6.

Example 2

The procedure is the same as in Example 1 with the exception that methyl iodide was substituted for 1-bromohexadecane.

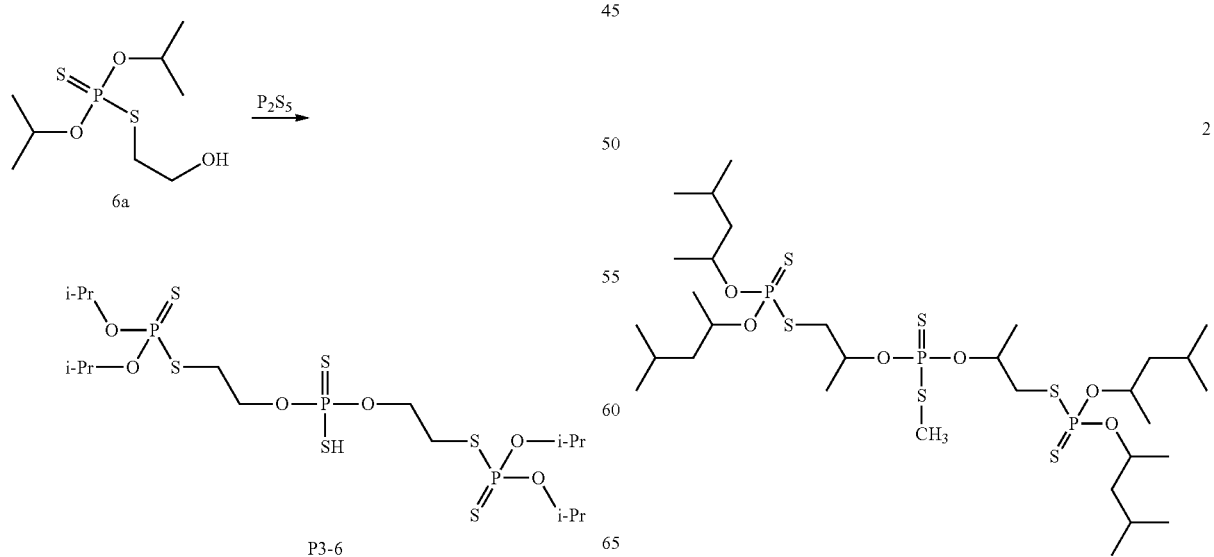

Example 3

A similar procedure to that described for Example 1 with the exception that benzyl bromide was substituted for 1-bromohexadecane.

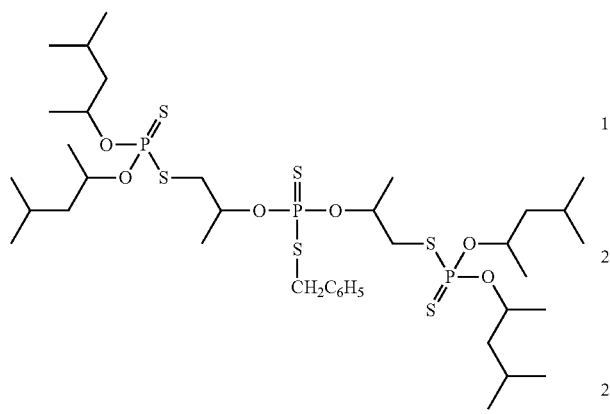

Example 4

To a stirring solution of P3-1 (161.4 g or 0.2 mol) at 60° C. was added vinyl butyl ether (20.0 g or 0.2 mol). The reaction mixture was left to stir at 60° C. for 11 hours under a nitrogen atmosphere. Subsequently, the unreacted vinyl butyl ether was removed under reduced pressure at 45° C.

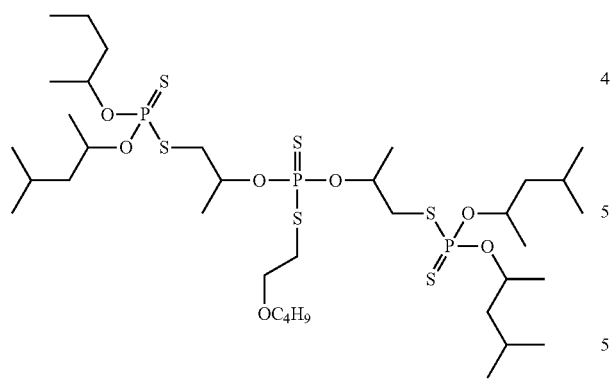

Example 5

To a stirring solution of P3-1 (109.8 g or 0.136 mol) at 60° C. was added ethyl acrylate (13.6 g or 0.136 mol). The reaction mixture was left to stir at 60° C. for 4 hours under a nitrogen atmosphere. Subsequently, the unreacted ethyl acrylate was removed under reduced pressure at 45° C.

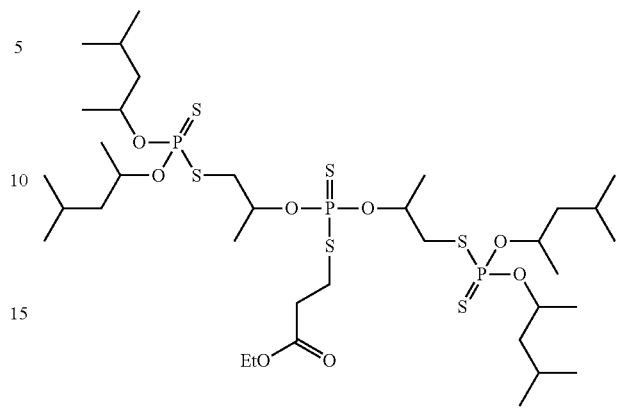

Example 5 was also prepared by reacting Intermediate 1a (897 g, 2.52 moles) with O,O-di-isopropyl dithiophosphoric acid (268 g, 1.25 moles; (used as supplied by Cheminova Inc., USA) in a round bottom flask equipped with a magnetic stirring bar. The reaction contents were heated to 85° C. under reduced pressure (10 mm Hg). Throughout the reaction isopropanol was distilled off and collected into a separate cooled vessel. After 14 hours the reaction contents were cooled to 10° C. and ethyl acrylate (130 g, 1.3 moles; Dow Chemical) was added to the reaction and the temperature was brought to 70° C. for 2 hours. Subsequently, the reaction was brought to 80° C. and a 100 mm Hg vacuum applied until ethyl acrylate no longer distilled off into the cold trap.

Example 6

To a stirring solution of P3-2 (872.4 g or 0.97 mol) at 45° C. was added 1,2-epoxydodecane (182.4 g or 0.97 mol). The reaction mixture was left to stir at 50° C. for 2 hours under a nitrogen atmosphere.

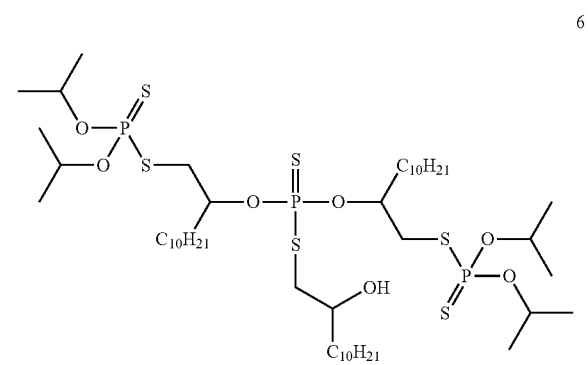

Example 7

To a stirring solution of P3-2 (986.4 g or 1.1 mol) at 60° C. was added ethyl acrylate (110.1 g or 1.1 mol). The reaction mixture was left to stir at 60° C. for 16 hours under a nitrogen atmosphere followed by a vacuum strip.

7

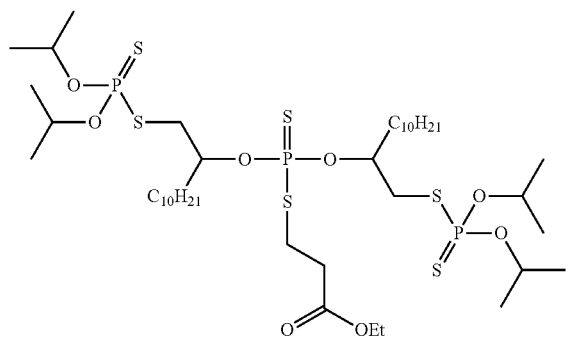

Example 8

To a stirring solution of P3-2 (980.4 g or 1.1 mol) at 60° C. was added acrylic acid (79.3 g or 1.1 mol). The reaction mixture was left to stir at 60° C. for 16 hours under a nitrogen atmosphere followed by a vacuum strip.

8

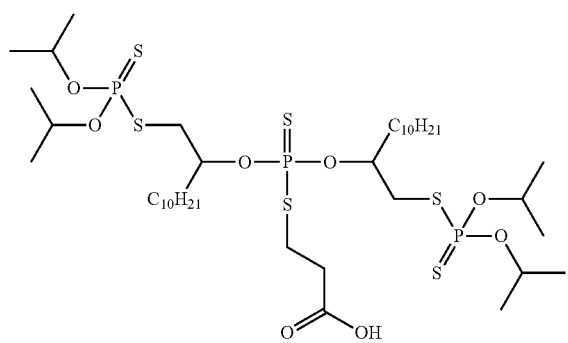

Example 9

To a stirring solution of P3-3 (852.2 g or 1.0 mol) at 40-50° C. was added 1,2-epoxydecane (156.1 g or 1.0 mol). The reaction mixture was left to stir at 50° C. for 2 hours under a nitrogen atmosphere.

9

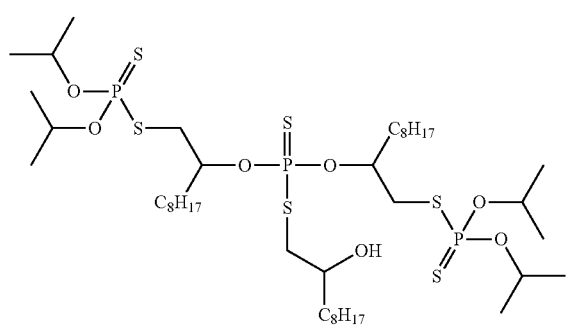

Example 10

To a stirring solution of P3-3 (91.9 g or 0.11 mol) at 60° C. was added ethyl acrylate (11.0 g or 0.11 mol). The reaction mixture was left to stir at 60° C. for 16 hours under a nitrogen atmosphere followed by a vacuum strip.

10

Example 11

To a stirring solution of P3-3 (91.9 g or 0.11 mol) at 40° C. was added 2-hydroxyethyl acrylate (12.1 g or 0.10 mol). The reaction mixture was left to stir at 40° C. for 16 hours under a nitrogen atmosphere followed by a vacuum strip.

11

Example 12

Reaction of P3-4 with ethyl acrylate as described for Example 10 to produce Example 12, which was subjected to a vacuum strip to remove any organic volatiles.

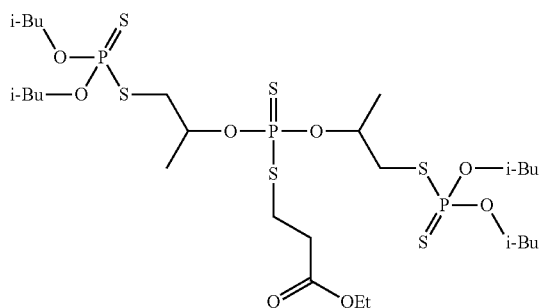

Example 13

Reaction of P3-5 with ethyl acrylate as described for Example 10 produced Example 13, which was subjected to a vacuum strip to remove any organic volatiles.

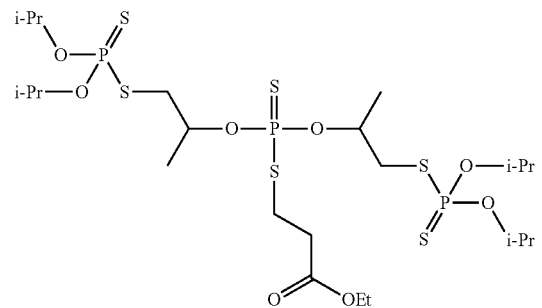

Example 13 was also prepared by an alternate synthesis. 0,0-di-isopropyl dithiophosphoric acid (1284 g, 6 moles) was added to a round bottom flask equipped with a magnetic stirring bar and cooled to 10° C. To this was slowly added propylene oxide (238 g, 4 moles) such that the reaction temperature never exceeded 20° C. Following the epoxide addition the reaction was left to stir at room temperature for 30 minutes before heating to 80° C. under vacuum for 18 hours. The reaction was then cooled to room temperature, ethyl acrylate (200 g, 2 moles) was added and the reaction contents brought to 70° C. for 2 hours. The colatiles were removed by bringing the reaction to 80° C. under vacuum for 2 hours.

Example 14

P3-6 was reacted with ethyl acrylate using the same procedure as for Example 10.

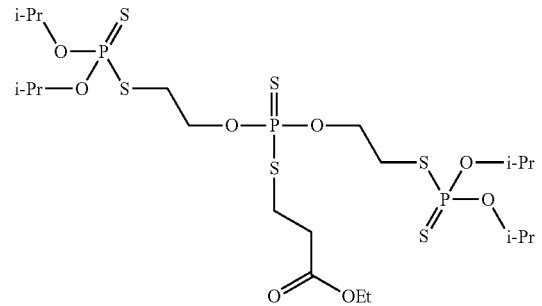

Example 14 was also made by an alternate synthesis wherein Intermediate 6a (3.1 g, 12 mmol) was combined with 0,0-di-isopropyl dithiophosphoric acid (1.36 g, 6.4 mmol) in a round bottom flask equipped with a magnetic stirring bar. The reaction contents were heated to 90° C. under reduced pressure (10 mm Hg) for 400 minutes. The reaction contents were cooled to room temperature, ethyl acrylate (0.7 g, 7 mmol) was added and the temperature brought to 70° C. for 2 hours. Subsequently, the reaction was brought to 80° C. and a 10 mm Hg vacuum applied until ethyl acrylate no longer distilled off into the cold trap. P NMR analysis of the reaction mixture revealed 77% compound 14.

Example 15

Compounds 15A and 15B were prepared by analogous procedures to Intermediate 6a, P3-6 and Example 14, except that 2-chloroethanol in the preparation of Intermediate 6a was replaced with 3-chloro-1-propanol and 6-chloro-1-hexanol for compounds 15A and 15B, respectively. Starting materials were purchased from Sigma Aldrich.

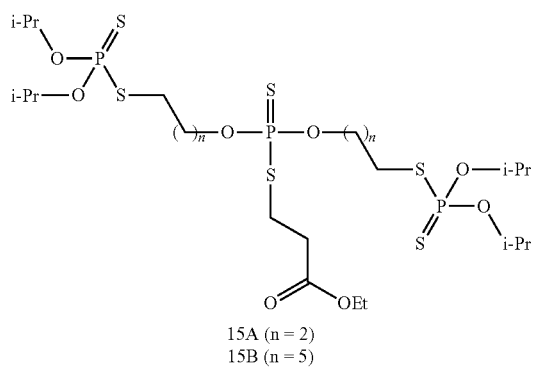

15A (n = 2)
15B (n = 5)

Example 16

Diisopropyl thiophosphoric acid can be obtained using the procedure described in J. Org. Chem. 76(10) 4189-4193, 2011. 1,2-epoxydecane (82.1 g, 0.525 mol; supplied by Arkema as Vikolox 10) was added to a round bottomed flask containing diisopropyl thiophosphoric acid (99.0 g, 0.5 mol) in 100 ml diethyl ether. The reaction temperature was maintained below 10° C. with the use of an ice bath during the epoxide addition. Following the addition the reaction mixture was allowed to warm to room temperature and stirred for two hours. At this time the diethyl ether was vacuum stripped. The crude reaction mixture was diluted with 200 ml of toluene and P2S5 (27.8 g, 0.125 mol) added to the flask. The reaction mixture was brought to 50° C. and stirred for 16 hours. At this time ethyl acrylate (25 g, 0.25 mol) was added to the flask and the reaction mixture cooked at 60° C. for 48 hours. The reaction mixture was filtered and the filtrate concentrated under reduced pressure. 31P NMR confirms compound 16.

16

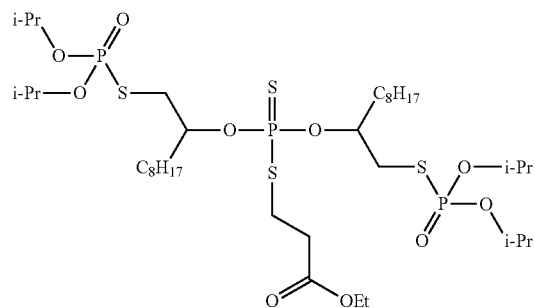

Example 17

2-tetradecyloxirane (31 g; supplied as Vikolox 16 from Arkema) was added to a solution of di-butyl phosphoric acid (24.4 g, 0.12 mol; supplied by Sigma Aldrich) in diethyl ether (50 g). The reaction flask was immersed in an ice bath and the epoxide addition rate was such that the internal reaction temperature did not exceed 10° C. Following the epoxide addition, the reaction mixture was stirred at room temperature for 4 hours followed by removal of diethyl ether under reduced pressure. The crude material so obtained was diluted with toluene (100 ml) followed by the addition of solid P2S5 (6.4 g, 0.029 mol). The reaction mixture was brought to 80° C. under vigorous stirring for 1 hour and then left to stir at ambient temperature for a further 16 hours. At this time ethyl acrylate (12 g, 0.12 mol) was added and the reaction mixture stirred at 60° C. for 3 hours. 31P NMR analysis confirms compound 17.

17

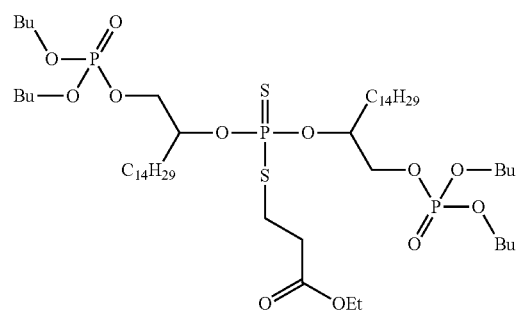

Example 18

Intermediate 1a (20.2 g, 0.057 mol), diethyl ether (150 ml) and oxyphosphorous trichloride (4.3 g, 0.028 mol) were combined in a round bottomed flask equipped with a magnetic stirring bar in that order at room temperature. Triethylamine (5.6 g, 0.055 mol) was introduced into the stirring mixture dropwise without any attempt to control temperature. The reaction was left to stir for 1 hour at which time a mixture of n-butanol (100 ml) and triethylamine (2.8 g, 0.028 mol) were added en masse. After stirring for 3 more hours a white precipitate was filtered off and the filtrate concentrated under reduced pressure. 31P NMR and LC-MS analysis confirms the formation of Compound 18.

18

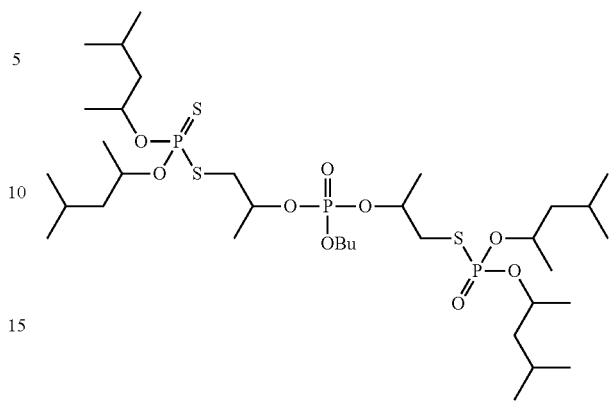

Example 19

Intermediate 1a (178.2 g, 0.5 mol) was added to a 1 L three necked round bottomed flask equipped with a mechanical stirrer, thermocouple and condenser under a nitrogen atmosphere. The internal temperature was brought to 70° C. and P205 (25.0 g, 0.176 mol) was added in five equal portions over a two hour period. The reaction mixture was cooked at a temperature of 70° C. for five hours prior to cooling to room temperature. Toluene (83 g) was added to the crude reaction mixture prior to filtration. The filter cake was washed with an additional 73 g of toluene and the filtrate was collected and concentrated under reduced pressure. 16.5 g of this material was split off and added to a 500 ml round bottomed flask containing acetonitrile (50 ml). To this was sequentially added triethylamine (4.0 g, 0.04 mol) and methyl iodide (8.5 g, 0.06 mol) under a nitrogen atmosphere. The reaction was left to stir at room temperature for 16 hours and then the acetonitrile was removed under reduced pressure. The white tacky solid so obtained was triturated with heptane (150 ml). The heptane containing layer was filtered and concentrated under reduced pressure to reveal a clear viscous liquid.

19

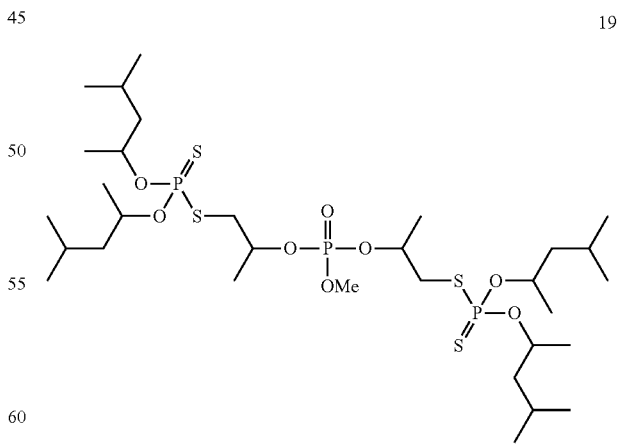

Example 20

Dibutyl phosphoric acid (31.5 g, 0.15 mol) was taken up in diethyl ether (100 ml) and the reaction mixture cooled in an ice bath. To this was added propylene oxide (9.3 g, 0.16 mol) at such a rate that the internal temperature never exceeded 20° C. After stirring for an additional one hour the reaction mixture was allowed to warm to room temperature and oxyphosphorous trichloride (11.5 g, 0.075 mol) and triethylamine (15.2 g, 0.15 mol) were added over a 15 minute period. The reaction was left to stir for one hour without any attempt to control temperature and then n-butanol (11.1 g, 0.15 mol) and triethylamine (7.6 g, 0.075 mol) were added en masse. The reaction was left to stir for 16 hours and then the solid precipitate was filtered off. The filtrate was sequentially washed with distilled water, saturated sodium carbonate and then brine. The organic fraction was dried over sodium sulfate, filtered and the filtrate concentrated under reduced pressure. LC-MS analysis confirms the formation of Compound 20.

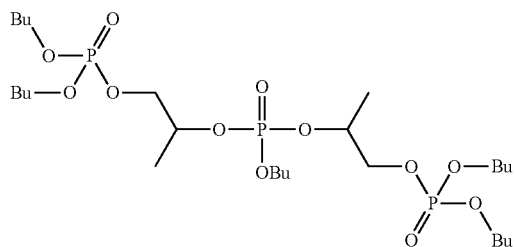

20

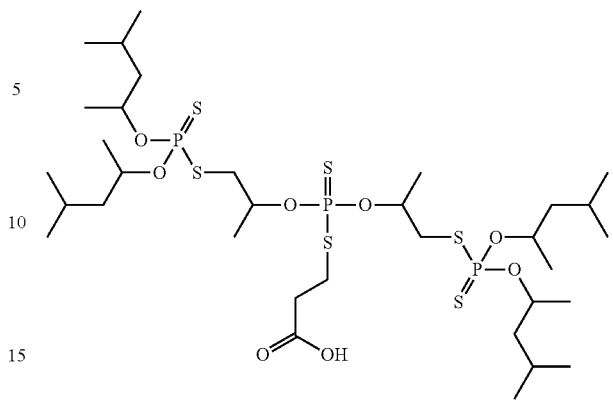

Example 21

To a stirring solution of P3-3 (852.2 g or 1.0 mol) at 40-50° C. was added methyl iodide (141.9 g or 1.0 mol). The reaction mixture was left to stir at 50° C. for 2 hours under a nitrogen atmosphere.

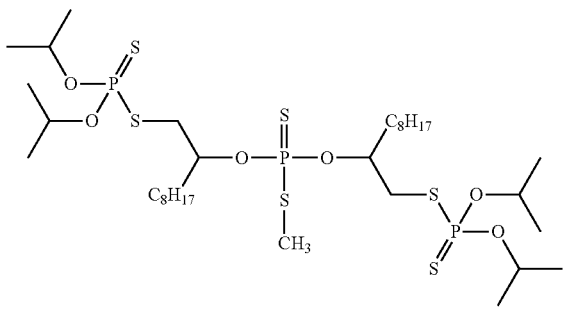

21

Example 22

To a stirring solution of P3-1 (109.8 g or 0.136 mol) at 60° C. was added 2-hydroxyethyl acrylate (12.1 g or 0.10 mol). The reaction mixture was left to stir at 60° C. for 4 hours under a nitrogen atmosphere followed by a vacuum strip.

Copper Corrosion Performance

To illustrate that the compounds of the present invention generally have improved copper corrosion performance relative to their respective intermediates, Example 21 and P3-3 were tested for copper corrosion performance in an ASTM D130 copper corrosion test run at 120° C. for 3 hours. Both samples were blended at 1 wt % in 150SN88VI. P3-3 rated a 4b whereas Example 21 rated an improved 2 C. The results of the copper corrosion test surprisingly show that the alkylation of the P—SH group of the P3-3 increased copper corrosion performance. Thus, while structurally similar to the compounds of the present invention, P3-3 did not exhibit the same copper corrosion performance as the compounds of the present invention.

Oxidative Stability

To illustrate that the compounds of the present invention generally have improved oxidative stability relative to their respective intermediates, neat compound P3-3, Example 21, neat compound P3-5, and Example 13 were analyzed by TGA-oxygen to determine the effect of a P—SH versus P—S-alkyl group on thermal stability. The TGA method is based off of ASTM E1131-08. The data are summarized in Table 1. The results of the oxidative stability test surprisingly show that the alkylation of the P—SH group of the P3-3 and the P3-5 increased oxidative stability. Thus, while structurally similar to the compounds of the present invention, P3-3 and P3-5 did not exhibit the same oxidative stability as the compounds of the present invention.

TABLE 1

| Examples | Temperature Midpoint of first Thermal Degradation Event (° C.) |
|---|---|
| P3-3 | 178.97 |
| Example 21 | 224.1 |
| P3-5 | 177.16 |
| Example 13 | 194.01 |

4 Ball Wear Scar, High Temperature-L37, and Verschleiss Testing

All of the Examples, as well as several comparative examples having a single phosphorus center, were subjected to Ball Wear Scar and High Temperature-L37. One example was tested in a Verschleiss wear test. The results are provided below in Tables 2a-2c.

TABLE 2a

Performance Summary: 4 Ball Wear Scar

| Examples | 4 Ball Wear Scar (mm) |
|---|---|
| Reference[1] | 0.75 |
| Example 1 | 0.449 |
| Example 2 | 0.449 |
| Example 3 | 0.436 |
| Example 4 | 0.355 |
| Example 5 | 0.359 |
| Example 6 | 0.449 |
| Example 7 | 0.368 |
| Example 8 | 0.338 |
| Example 9 | 0.428 |
| Example 10 | 0.355 |
| Example 11 | 0.393 |
| Example 12 | 0.377 |
| Example 13 | 0.359 |
| Example 14 | 0.333 |
| Example 15, n = 2 | 0.385 |
| Example 15, n = 5 | 0.406 |
| Example 16 | 0.603 |
| Example 17 | 0.436 |
| Example 18 | 0.432 |
| Example 19 | 0.633 |
| Example 20 | 0.552 |
| Comparative Example A | 0.402 |

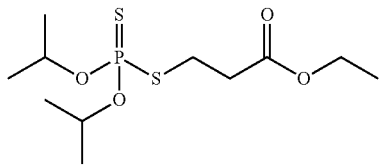 [SMILES: CCOC(=O)CCSP(=S)(OC(C)C)OC(C)C]

[1]Reference contains base oil without added anti-wear agent.

Conditions for 4 Ball Wear Scar Test: 1200 rpm, 40 Kg, 75° C. and 1 hour duration. The anti-wear components were tested at 1100 ppm phosphorus in an Exxon Mobil Group I base stock (80W-90). The conditions of the 4-ball wear scar determination were in accordance with ASTM method D4172 (1200 rpm, 40 KG, 75° C., 1 hr).

TABLE 2b

Performance Summary: High Temperature L-37

| Examples | High Temperature L-37 |
|---|---|
| Reference[1] | Fail |
| Example 5 | Pass |
| Example 6 | Pass |
| Example 9 | Pass |
| Example 10 | Pass |
| Comparative Example A | Fail |

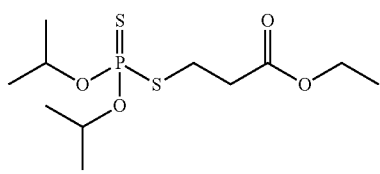 [SMILES: CCOC(=O)CCSP(=S)(OC(C)C)OC(C)C]

TABLE 2b-continued

Performance Summary: High Temperature L-37

| Examples | High Temperature L-37 |
|---|---|
| Comparative Example B | Fail |

(structure shown)

| Comparative Example C | Fail |

(structure shown with $C_{10}H_{21}$)

The test samples above were subjected to the High Temperature L-37 test (according to ASTM D-6121), modified to test the lubricant at 325° F. The HT L-37 is used to determine the load-carrying, wear, and extreme pressure characteristics of gear lubricants in hypoid axle assemblies under conditions of high-speed, low-torque, and low-speed, high-torque operation. The procedure's apparatus includes a rear axle assembly, an engine, a transmission, and two large dynamometers. The axle is operated for 100 minutes at 440 axle rpm, 295° F. lubricant temperature, and 9460 lb-in. of torque. The axle is then operated for 16 hours at 80 axle rpm, 325° F. lubricant temperature, and 41,800 lb-in. of torque. The pass/fail criteria require that there be no "significant" distress to the ring and pinion gears in several different wear categories, including wear, rippling, ridging, spalling and scoring.

In Table 2b above, test results for formulations containing Compounds 5, 6, 9 and 10 show that the gear distress was identified by a "pass" test result. A "pass" indicates that significant gear distress was not observed at the end of test. Thus, there was not a significant amount of iron detected in the test sample after completion of the test. When iron is present in the end of test fluid in significant amounts, it is evidence of gear distress and loss of anti-wear protection. All finished fluids used for HT-L37 testing contained sufficient anti-wear to deliver 1100 ppm phosphorus to the finished fluid. The finished fluids only differed in the anti-wear component present, but otherwise contained identical formulations of typical axle componentry and base stock. The formulations for the HT-L-37 testing contained 3.24% sulfurized isobutylene, 1.4% of a pour point depressant, 1% boronated maleated bis-succinimide dispersant made with 1300 MW polyisobutylene, 0.15% 2,5-(t-nonylthio)-1,3,4-thiadiazole, 0.05% antifoam, 0.005% dimer acid, 1.15% antiwear compound of the present invention, and the balance was a base oil mixture of 150N and 2500N from Exxon-Mobil in a 35:54 ratio. The 150N has a kinematic viscosity at 40° C. of 29-32 m²/sec. And the 2500N has a kinematic viscosity at 100° C. of 30.6-32.7 mm²/sec. The finished fluid including the base oils and the additive components had a kinematic viscosity at 100° C. of 15.5 cSt.

TABLE 2c

Performance Summary: Verschleiss

| Example | Verschleiss |
|---|---|
| Example 7 | 29 mg |

The Verschleiss test method follows ZF Specification AA05.468.017 issued in 2005. The FZG Verschleiss test is a low speed test used to determine the end of test iron content, which represents the amount of metal gear material lost from the gear as a result of wear. New standard FZG C pitting gears were used for each test. The gears had a tooth thickness of 14 mm, a center distance of 91.5 mm and a roughness of 0.3+/−0.1 μm. Tests were conducted at room temperature with no preheating. The testing procedure utilized three 40 hour cycles to determine gear wear. Each cycle had a pinion speed of 13 rpm and a pressure of 1814 N/mm2. Cycles 1 and 3 were conducted at 90° C., and cycle 2 was conducted at 120° C. Gears were weighed prior to the test to the nearest milligram. Gears were subsequently weighed after each cycle, cleaned sequentially with Stoddard solvent, acetone, and pentane, and then placed in a desiccator for 1 hour to stabilize. Each gear was thus weighed three times. The cleaning cycle was repeated until 2 consecutive weightings were the same.

The finished fluid used for FZG Verschleiss testing contained sufficient anti-wear component to deliver 1100 ppm phosphorus to the finished fluid. In particular, the formulation contained 3.46% sulfurized isobutylene, 1.82% of a pour point depressant, 1.07% dispersant, 0.125% thiadiazole derivative, 0.25% antioxidant, 0.05% antifoam, 0.005% dimer acid, 1.2% antiwear compound of present invention, and the balance base oil.

Other embodiments of the present disclosure will be apparent to those skilled in the art from consideration of the specification and practice of the embodiments disclosed and suggested herein. It is intended that the specification and examples be considered as exemplary only, with a true scope and spirit of the disclosure being indicated by the following claims.

The invention claimed is:

1. A compound of Formula (I)

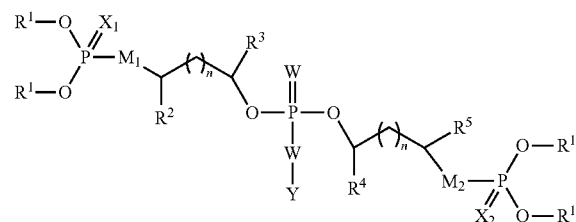

(I)

wherein each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
$M_1$, $M_2$, $X_1$, and $X_2$ are each independently S or O;
each W is independently S or O;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

2. The compound of claim 1, wherein $X_1$ is S.
3. The compound of claim 1, wherein $X_2$ is S.
4. The compound of claim 1, wherein $M_1$ is S.
5. The compound of claim 1, wherein $M_2$ is S.
6. The compound of claim 1, wherein $X_1$, $X_2$, $M_1$, and $M_2$ are each S.
7. The compound of claim 1, wherein $X_1$ is O.
8. The compound of claim 1, wherein $X_2$ is O.
9. The compound of claim 1, wherein $M_1$ is O.
10. The compound of claim 1, wherein $M_2$ is O.
11. The compound of claim 1, wherein $X_1$, $X_2$, $M_1$, and $M_2$ are each O.
12. The compound of claim 1, wherein $X_1$ and $X_2$ are O and $M_1$ and $M_2$ are S.
13. The compound of claim 1, wherein $X_1$ and $X_2$ are S and $M_1$ and $M_2$ are O.
14. The compound of claim 1, selected from the group consisting of

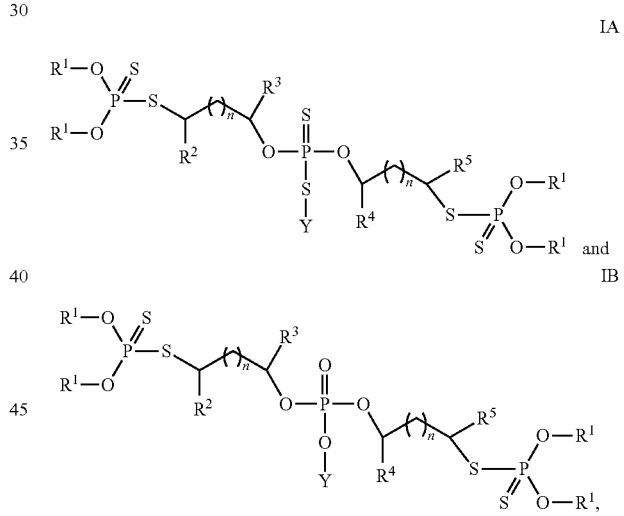

wherein each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxyalkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxyalkylene, hydroxyalkyleneoxy, hydroxyl and alkoxy; and
$R^9$ is alkyl.

15. The compound of claim 1, wherein each $R^2$ $R^3$, $R^4$ and $R^5$ is independently selected from hydrogen or $C_1$-$C_{30}$ alkyl.
16. The compound of claim 1, wherein at least one of $R^2$ and $R^3$ is hydrogen and at least one of $R^4$ and $R^5$ is hydrogen.

17. The compound of claim 1, wherein each $R^1$ is the same.

18. The compound of claim 1, wherein Y is $O_1$—$C_{20}$alkyl.

19. The compound of claim 1, wherein Y is —$R^6$—$R^7$—$R^8$.

20. The compound of claim 1, wherein $R^3$ and $R^4$ are the same.

21. The compound of claim 1, wherein $R^2$ and $R^5$ are the same.

22. The compound of claim 1, wherein $R^2$ and $R^4$ are the same.

23. The compound of claim 1, wherein $R^3$ and $R^5$ are the same.

24. The compound of claim 1, wherein $R^2$ and $R^5$ are both hydrogen.

25. The compound of claim 1, wherein $R^1$ is $C_3$-$C_{10}$alkyl.

26. The compound of claim 25, wherein $R^1$ is $C_3$-$C_6$alkyl.

27. The compound of claim 1, wherein one of $R^2$ and $R^3$ and one of $R^4$ and $R^5$ is $C_1$-$C_{10}$ alkyl.

28. The compound of claim 1, wherein the compound is selected from the group consisting of:

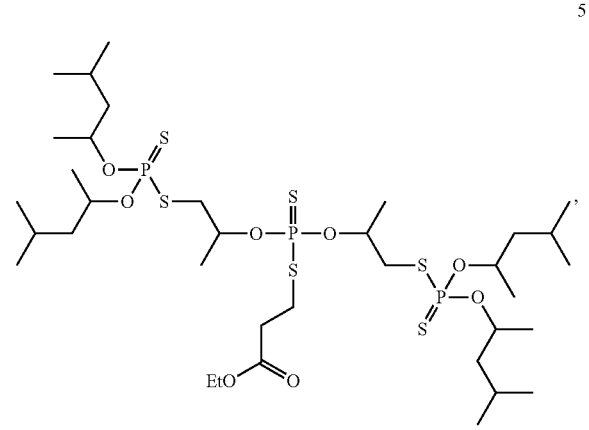 [SMILES: CC(C)CC(C)OP(=S)(OC(C)CC(C)C)SCC(C)OP(=S)(OC(C)CSP(=S)(OC(C)CC(C)C)OC(C)CC(C)C)SCCC(=O)O]

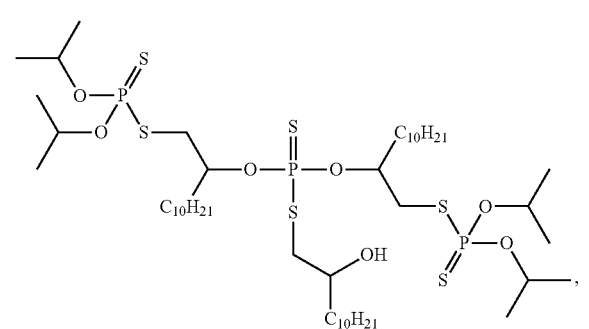

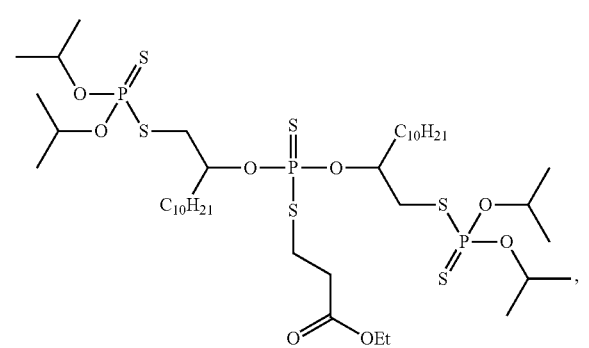

-continued

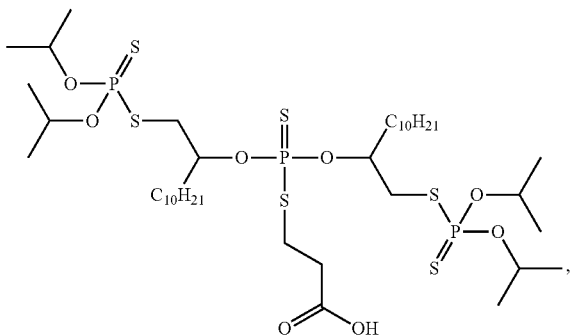

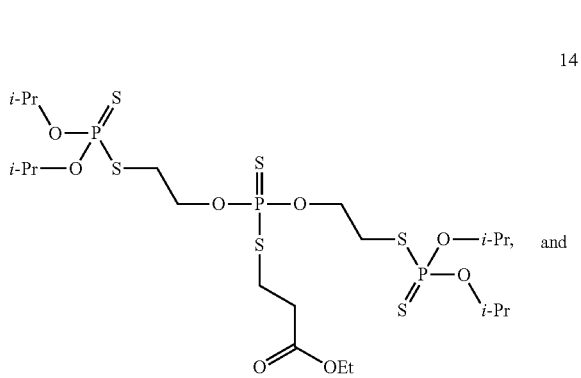

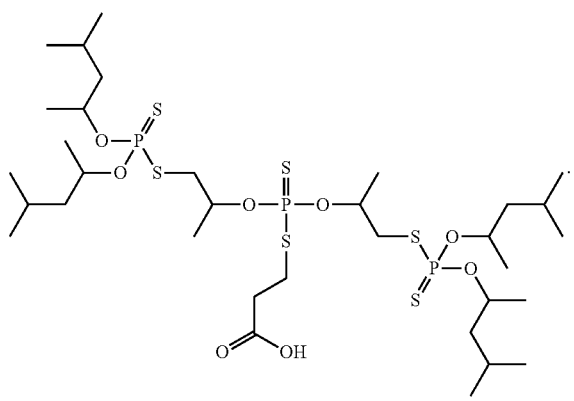
29. The compound of claim 1, wherein the compound is selected from the group consisting of:
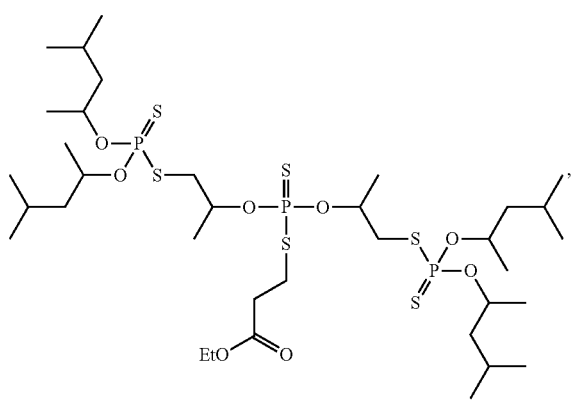
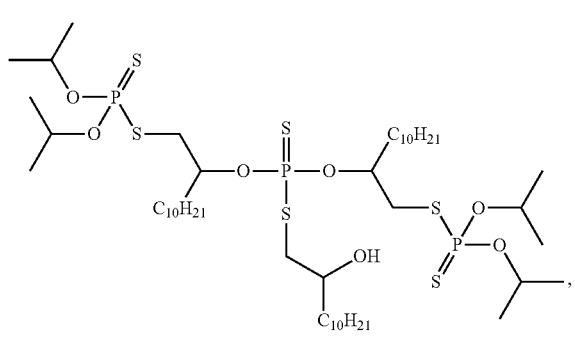
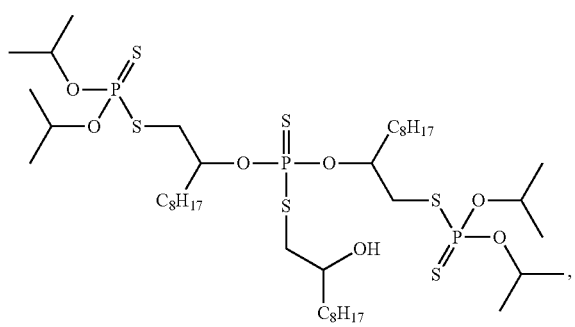
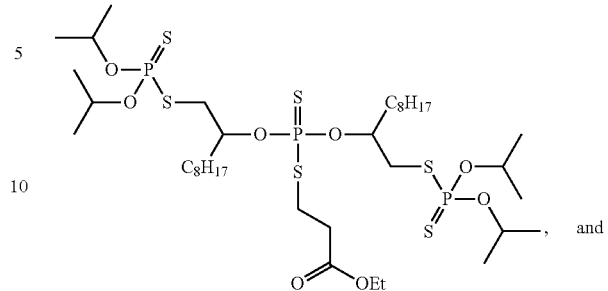, and
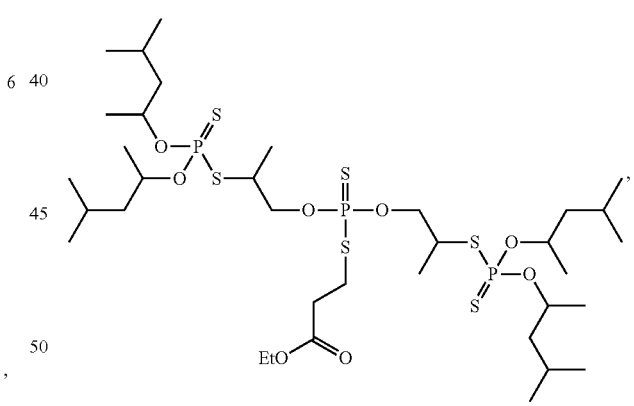
30. The compound of claim 1, wherein the compound is selected from the group consisting of:
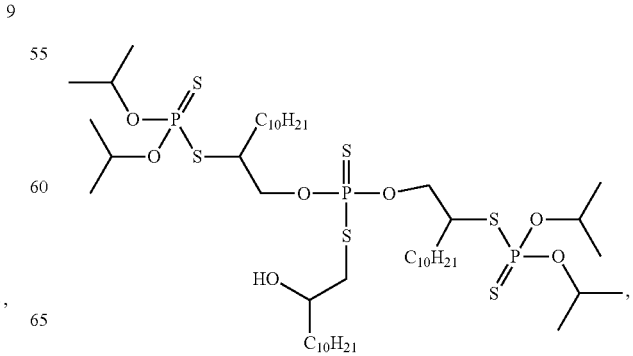

-continued
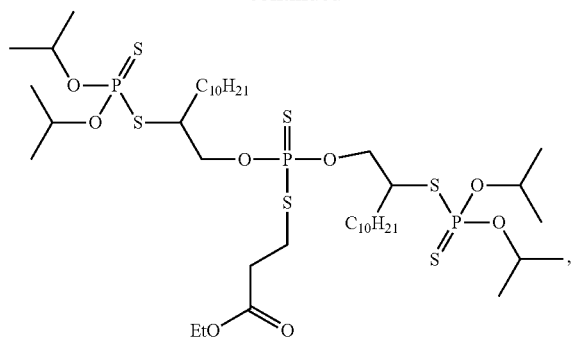
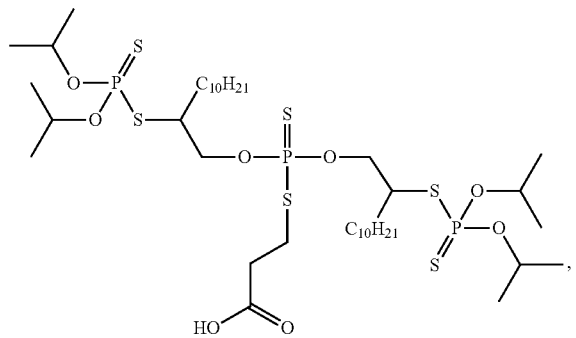
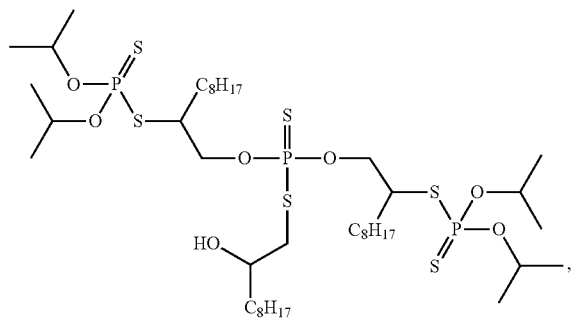
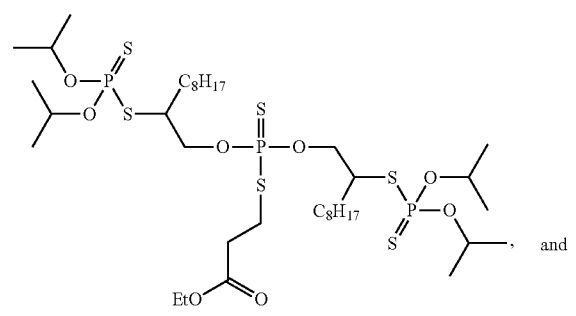
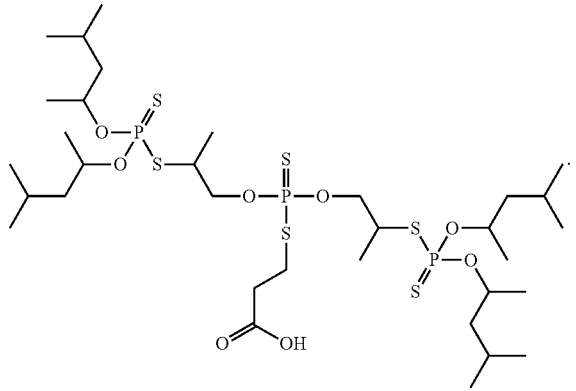
and
31. The compound of claim 1, wherein the compound is selected from the group consisting of:
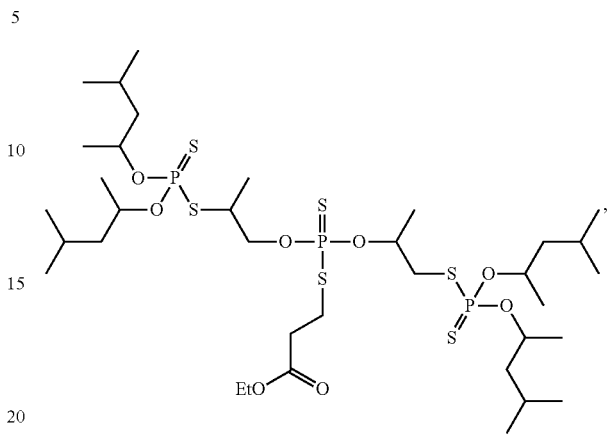
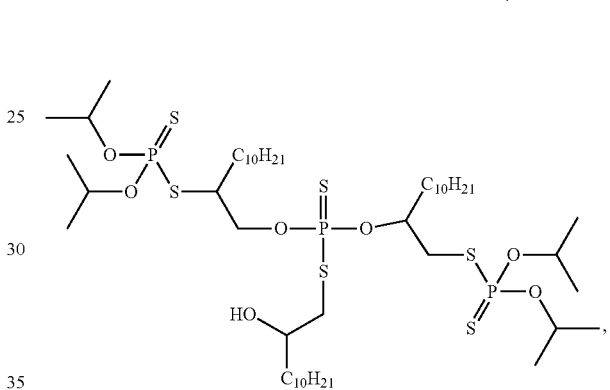

-continued

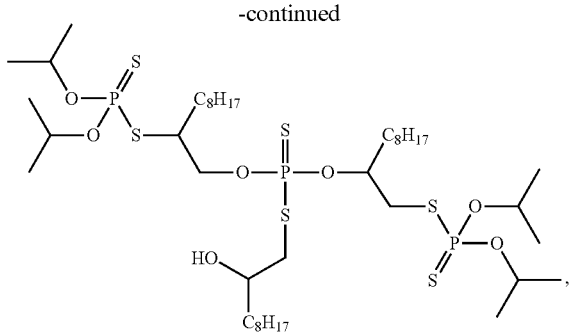

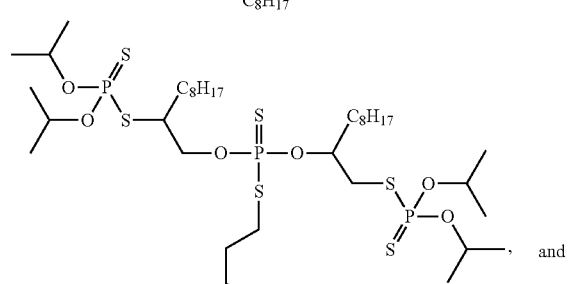

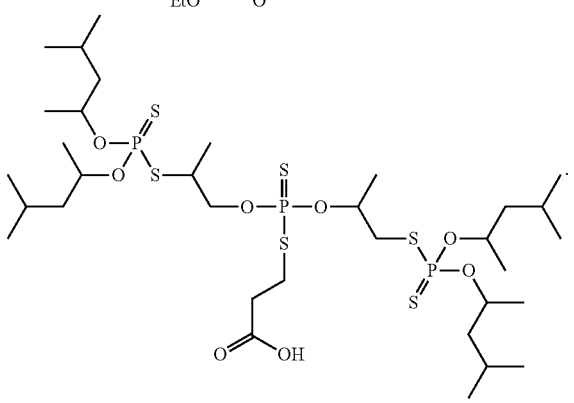

32. A compound prepared by reacting a compound of the formula:

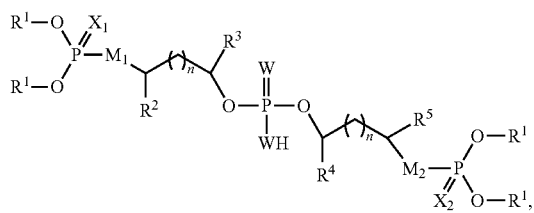

with a reactive group to form a compound of the structure

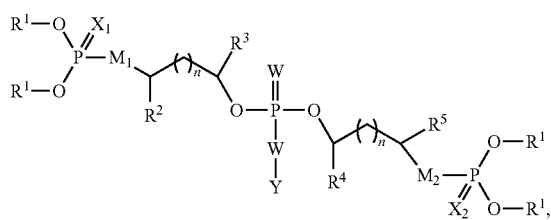

wherein each W is independently S or O;
$M_1$, $M_2$, $X_1$, and $X_2$ are each independently S or O;
each $R^1$ is independently alkyl or cycloalkyl;
each $R^2$ $R^3$, $R^4$ and $R^5$ is independently selected from the group consisting of hydrogen, alkyl and cycloalkyl;
each n is independently an integer from 0 to 6;
Y is selected from the group consisting of alkyl, alkoxy-alkylene, benzyl, and —$R^6$—$R^7$—$R^8$;
$R^6$ is alkylene;
$R^7$ is selected from the group consisting of a bond, alkylene; —C(O)— and —C($R^9$)—;
$R^8$ is selected from the group consisting of alkyl, hydroxy-alkylene, hydroxyalkyleneoxy, hydroxyl and alkoxy; and
$R^9$ is alkyl.

33. A compound prepared by a process comprising:
(a) reacting a compound of the formula:

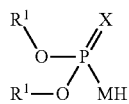

with an epoxide of the formula

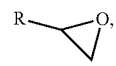

wherein R is alkyl or cycloalkyl; and
M and X are each independently S or O;
(b) reacting the reaction product of step (a) with $P_2W_5$, to form a compound of the structure

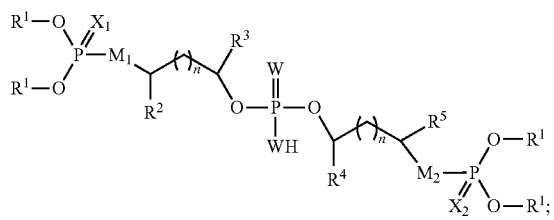

and
(c) reacting the reaction product of step (b) with a reactive group to form a compound of the structure

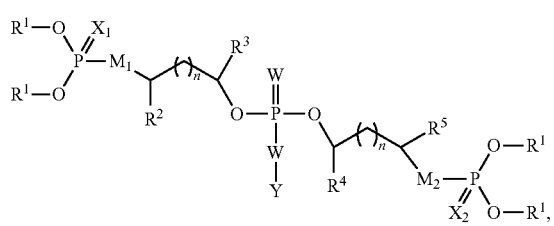

wherein each W is the same and is either S or O;
each $R^1$ is independently alkyl or cycloalkyl;
each $R^2$ $R^3$, $R^4$ and $R^5$ is independently selected from the group consisting of hydrogen, alkyl and cycloalkyl;
n is 0;
Y is selected from the group consisting of alkyl, alkoxy-alkylene, benzyl, and —$R^6$—$R^7$—$R^8$;

$R^6$ is alkylene;

$R^7$ is selected from the group consisting of a bond, alkylene; —C(O)— and —C($R^9$)—;

$R^8$ is selected from the group consisting of alkyl, hydroxyalkylene, hydroxyalkyleneoxy, hydroxyl and alkoxy; and $R^9$ is hydroxyl.

34. A lubricant additive composition comprising a compound of claim 1.

35. The lubricant additive composition of claim 34, wherein the lubricant additive composition further comprises one or more additive components selected from the group consisting of an antioxidant, antiwear agents, corrosion inhibitor, detergent, extreme pressure agent, dispersant, viscosity index improvers, and friction modifiers.

36. A lubricant composition comprising:
a) a majority base oil; and
b) a compound as claimed in claim 1.

37. The lubricant composition of claim 36, wherein the lubricant composition further comprises one or more additive components selected from the group consisting of an antioxidant, antiwear agents, corrosion inhibitor, detergent, extreme pressure agent, dispersant, viscosity index improvers, and friction modifiers.

38. The lubricant composition of claim 37 wherein the compound of Formula (I) is present in an amount from about 0.010 wt % to about 5 wt % based on the total weight of the lubricant composition.

39. The lubricant composition of claim 38, wherein the compound of Formula (I) is present in an amount from about 0.05 wt % to about 2.0 wt % based on the total weight of the lubricant composition.

40. A method of lubricating moving metal surfaces comprising lubricating the metal surfaces with a lubricant composition of claim 36.

41. The method of claim 40, wherein the metal surfaces are a machine part.

42. The method of claim 41 wherein the machine part is selected from one or more of a gear, an axle, a differential, an engine, a crankshaft, a transmission, a clutch, a hydraulic apparatus, a slideway apparatus, and a turbine.

43. A method of reducing wear between moving metal surfaces of a machine part comprising lubricating the machine part with a lubricant composition comprising:
a) a major amount of an oil of lubricating viscosity;
b) an effective amount of a compound of claim 1.

44. A method of increasing oxidative stability of a lubricating composition comprising adding to the lubricating composition an effective amount of a compound as claimed in claim 1.

* * * * *